(12) United States Patent
Rockley et al.

(10) Patent No.: US 11,338,139 B2
(45) Date of Patent: May 24, 2022

(54) SYSTEM AND METHODS FOR CONTROLLED ELECTRICAL MODULATION FOR VISION THERAPY

(71) Applicant: BIOVISICS MEDICAL, LLC, Delano, MN (US)

(72) Inventors: Paul Rockley, Corona Del Mar, CA (US); Thomas W. Harold, Prior Lake, MN (US); James R. Chiapetta, Delano, MN (US)

(73) Assignee: Biovisics Medical, Inc., Delano, MN (US)

( * ) Notice: Subject to any disclaimer, the term of this patent is extended or adjusted under 35 U.S.C. 154(b) by 97 days.

(21) Appl. No.: 16/589,383

(22) Filed: Oct. 1, 2019

(65) Prior Publication Data
US 2020/0101290 A1    Apr. 2, 2020

Related U.S. Application Data

(60) Provisional application No. 62/739,810, filed on Oct. 1, 2018.

(51) Int. Cl.
*A61N 1/36* (2006.01)
*A61N 1/04* (2006.01)

(52) U.S. Cl.
CPC ....... *A61N 1/36046* (2013.01); *A61N 1/0484* (2013.01); *A61N 1/36031* (2017.08)

(58) Field of Classification Search
None
See application file for complete search history.

(56) References Cited

U.S. PATENT DOCUMENTS

| | | | |
|---|---|---|---|
| 2,283,752 | A | 5/1942 | Gonsett |
| 2,527,947 | A | 10/1950 | Loos |
| 2,760,483 | A | 8/1956 | Tassicker |
| 3,376,870 | A | 4/1968 | Yamamoto et al. |
| 3,669,119 | A | 6/1972 | Symmes |
| D246,529 | S | 11/1977 | Willard |
| 4,162,542 | A | 7/1979 | Frank |
| D280,670 | S | 9/1985 | Fireman |
| 4,551,149 | A | 11/1985 | Scairra |
| 4,614,193 | A | 9/1986 | Liss et al. |

(Continued)

FOREIGN PATENT DOCUMENTS

| | | |
|---|---|---|
| CN | 1096460 A | 12/1994 |
| DE | 202012003100 U1 | 10/2012 |

(Continued)

OTHER PUBLICATIONS

Invitation to Pay Additional Fees dated Feb. 14, 2020 for International Application No. PCT/US2019/063580.

(Continued)

*Primary Examiner* — Brian T Gedeon
(74) *Attorney, Agent, or Firm* — Seager, Tufte & Wickhem, LLP

(57) ABSTRACT

Illustrative methods and devices for providing stimulus to the eye to treat vision disorders. Systems and methods for feedback relating to the stimulus itself as well as the effect of such stimulus on the patient are provided. Various examples may include therapies for vision disorders that can progress to blindness, such as macular degeneration or other diseases and disease processes.

15 Claims, 8 Drawing Sheets

(56) References Cited

U.S. PATENT DOCUMENTS

| | | |
|---|---|---|
| 4,628,933 A | 12/1986 | Michelson |
| 4,664,117 A | 5/1987 | Beck |
| 4,712,558 A | 12/1987 | Kidd et al. |
| 4,979,811 A | 12/1990 | Boyer |
| 5,024,223 A | 6/1991 | Chow |
| 5,109,844 A | 5/1992 | De Juan, Jr. et al. |
| 5,147,284 A | 9/1992 | Fedorov et al. |
| 5,154,174 A | 10/1992 | Hawlina |
| 5,193,540 A | 3/1993 | Schulman et al. |
| 5,263,200 A | 11/1993 | Miller |
| 5,522,864 A | 6/1996 | Wallace et al. |
| 5,556,423 A | 9/1996 | Chow et al. |
| 5,597,381 A | 1/1997 | Rizzo, III |
| 5,643,330 A | 7/1997 | Holsheimer et al. |
| 5,836,996 A | 11/1998 | Doorish |
| 5,843,147 A | 12/1998 | Testerman et al. |
| 5,865,839 A | 2/1999 | Doorish |
| 5,873,901 A | 2/1999 | Wu et al. |
| 5,895,415 A | 4/1999 | Chow et al. |
| 5,935,155 A | 8/1999 | Humayun et al. |
| 5,944,747 A | 8/1999 | Greenberg et al. |
| 6,007,532 A | 12/1999 | Netherly |
| D421,124 S | 2/2000 | Yavitz |
| 6,035,236 A | 3/2000 | Jarding et al. |
| D425,623 S | 5/2000 | Funk |
| D429,817 S | 8/2000 | Banks |
| 6,101,411 A | 8/2000 | Newsome |
| 6,131,208 A | 10/2000 | Banks |
| 6,154,671 A | 11/2000 | Parel et al. |
| 6,168,593 B1 * | 1/2001 | Sharkey ............... A61B 18/148 606/34 |
| D440,660 S | 4/2001 | Sternberg |
| 6,230,057 B1 | 5/2001 | Chow et al. |
| D444,561 S | 7/2001 | Stein |
| 6,275,735 B1 | 8/2001 | Jarding et al. |
| 6,282,449 B1 | 8/2001 | Kamerling et al. |
| 6,306,075 B1 | 10/2001 | Shadduck |
| 6,324,429 B1 | 11/2001 | Shire et al. |
| 6,389,317 B1 | 5/2002 | Chow et al. |
| 6,400,989 B1 | 6/2002 | Eckmiller |
| 6,408,211 B1 | 6/2002 | Powell |
| 6,424,864 B1 | 7/2002 | Matsuura |
| 6,442,431 B1 | 8/2002 | Veraart et al. |
| 6,458,157 B1 | 10/2002 | Suaning |
| 6,515,227 B1 | 2/2003 | Massey et al. |
| 6,611,716 B2 | 8/2003 | Chow et al. |
| 6,755,530 B1 | 6/2004 | Loftus et al. |
| 6,792,314 B2 | 9/2004 | Byers et al. |
| 6,976,998 B2 | 12/2005 | Rizzo et al. |
| 6,990,377 B2 | 1/2006 | Gliner et al. |
| 7,001,608 B2 | 2/2006 | Fishman et al. |
| 7,003,354 B2 | 2/2006 | Chow et al. |
| 7,006,873 B2 | 2/2006 | Chow et al. |
| 7,031,776 B2 | 4/2006 | Chow et al. |
| 7,037,943 B2 | 5/2006 | Peyman |
| 7,043,308 B2 | 5/2006 | Cohen |
| 7,047,080 B2 | 5/2006 | Palanker et al. |
| 7,058,455 B2 | 6/2006 | Huie, Jr. et al. |
| 7,067,327 B2 | 6/2006 | Wu et al. |
| 7,130,693 B1 | 10/2006 | Montalbo |
| 7,139,612 B2 | 11/2006 | Chow et al. |
| 7,146,209 B2 | 12/2006 | Gross et al. |
| 7,147,865 B2 | 12/2006 | Fishman et al. |
| 7,158,834 B2 | 1/2007 | Paul, Jr. |
| 7,158,836 B2 | 1/2007 | Suzuki |
| 7,248,928 B2 | 7/2007 | Yagi |
| 7,251,528 B2 | 7/2007 | Harold |
| 7,306,621 B1 | 12/2007 | Halla et al. |
| 7,321,796 B2 | 1/2008 | Fink et al. |
| 7,337,008 B2 | 2/2008 | Terasawa et al. |
| 7,398,124 B2 | 7/2008 | Fujikado et al. |
| 7,400,021 B2 | 7/2008 | Wu et al. |
| 7,447,547 B2 | 11/2008 | Palanker |
| 7,447,548 B2 | 11/2008 | Eckmiller |
| 7,458,456 B2 | 12/2008 | Hogan et al. |
| 7,556,621 B2 | 7/2009 | Palanker et al. |
| 7,877,148 B2 | 1/2011 | Chowdhury et al. |
| 7,883,535 B2 | 2/2011 | Cantin et al. |
| 7,974,699 B2 | 7/2011 | Tano et al. |
| 7,979,134 B2 | 7/2011 | Chow et al. |
| 7,981,062 B2 | 7/2011 | Chow et al. |
| 8,000,804 B1 | 8/2011 | Wessendorf et al. |
| 8,039,445 B2 | 10/2011 | Behar-Cohen et al. |
| 8,070,688 B2 | 12/2011 | Livne et al. |
| 8,190,266 B2 | 5/2012 | Ameri et al. |
| 8,197,539 B2 | 6/2012 | Nasiatka et al. |
| 8,260,428 B2 | 9/2012 | Fink et al. |
| 8,265,764 B2 | 9/2012 | Tano et al. |
| 8,306,626 B2 | 11/2012 | Chow et al. |
| 8,377,120 B2 | 2/2013 | Lipshitz et al. |
| 8,396,561 B2 | 3/2013 | Pezaris et al. |
| 8,396,562 B2 | 3/2013 | Ameri et al. |
| 8,398,692 B2 | 3/2013 | Deisseroth et al. |
| 8,433,417 B2 | 4/2013 | Flood |
| 8,478,415 B1 | 7/2013 | Halla et al. |
| 8,515,548 B2 | 8/2013 | Rofougaran et al. |
| 8,612,002 B2 | 12/2013 | Faltys et al. |
| 8,634,923 B2 | 1/2014 | Sharpee et al. |
| 8,639,345 B2 | 1/2014 | Eipper et al. |
| 8,691,877 B2 | 4/2014 | Yun et al. |
| 8,700,167 B2 | 4/2014 | Sabel |
| 8,725,266 B2 | 5/2014 | Olson et al. |
| 8,731,683 B2 | 5/2014 | Lindenthaler |
| 8,734,513 B2 | 5/2014 | Wu et al. |
| 8,771,349 B2 | 7/2014 | Schachar |
| 8,788,041 B2 | 7/2014 | Yun et al. |
| 8,801,942 B2 | 8/2014 | Scorsone et al. |
| 8,824,156 B2 | 9/2014 | Tai et al. |
| 8,852,290 B2 | 10/2014 | Rowley et al. |
| 8,864,805 B2 | 10/2014 | Deisseroth et al. |
| 8,868,202 B2 | 10/2014 | Della Santina et al. |
| 8,903,495 B2 | 12/2014 | Greenberg et al. |
| 8,909,340 B2 | 12/2014 | Yun |
| 8,918,186 B2 | 12/2014 | Tiedtke |
| 8,918,188 B2 | 12/2014 | Tiedtke |
| 8,972,004 B2 | 3/2015 | Simon et al. |
| 9,002,463 B2 | 4/2015 | Tiedtke |
| 9,037,251 B2 | 5/2015 | Narayan et al. |
| 9,037,252 B2 | 5/2015 | Tiedtke |
| 9,037,255 B2 | 5/2015 | Rocke et al. |
| 9,078,743 B2 | 7/2015 | Tai et al. |
| 9,079,042 B2 | 7/2015 | Tiedtke et al. |
| 9,125,734 B2 | 9/2015 | Keller et al. |
| 9,144,608 B2 | 9/2015 | Olson et al. |
| 9,162,060 B2 | 10/2015 | Wrobel et al. |
| 9,162,061 B2 | 10/2015 | Barnes |
| 9,180,309 B2 | 11/2015 | Nirenberg et al. |
| 9,186,523 B1 | 11/2015 | Zolli |
| 9,187,745 B2 | 11/2015 | Deisseroth et al. |
| 9,199,080 B2 | 12/2015 | Gekeler et al. |
| 9,220,634 B2 | 12/2015 | Nirenberg |
| 9,220,894 B1 | 12/2015 | Zhu |
| 9,233,026 B2 | 1/2016 | Ziemeck et al. |
| 9,233,258 B2 | 1/2016 | Simon et al. |
| 9,242,067 B2 | 1/2016 | Shore et al. |
| 9,403,001 B2 | 1/2016 | Simon et al. |
| 9,302,103 B1 | 4/2016 | Nirenberg |
| 9,322,713 B2 | 4/2016 | Narayan et al. |
| 9,326,887 B2 | 5/2016 | Yun |
| 9,339,650 B2 | 5/2016 | Rezai et al. |
| 9,345,568 B2 | 5/2016 | Cho et al. |
| 9,370,348 B2 | 6/2016 | Tally et al. |
| 9,381,355 B2 | 7/2016 | Khraiche et al. |
| 9,452,289 B2 | 9/2016 | Chichilnisky et al. |
| 9,456,836 B2 | 10/2016 | Boling et al. |
| 9,468,760 B1 | 10/2016 | Lin |
| 9,498,380 B2 | 11/2016 | Berdahl et al. |
| 9,630,013 B2 | 4/2017 | Bachinski et al. |
| 9,636,212 B2 | 5/2017 | Tiedtke et al. |
| 9,682,232 B2 | 6/2017 | Shore et al. |
| 9,687,652 B2 | 6/2017 | Franke et al. |
| 9,697,746 B2 | 7/2017 | Barnes et al. |
| 9,737,710 B2 | 8/2017 | Fan |
| 9,737,711 B2 | 8/2017 | Twyford et al. |

(56) References Cited

U.S. PATENT DOCUMENTS

| | | | |
|---|---|---|---|
| 9,789,312 B2 | 10/2017 | Fukuma et al. | |
| 9,795,787 B2 | 10/2017 | Cho et al. | |
| 9,821,003 B2 | 11/2017 | Yun | |
| 9,821,159 B2 | 11/2017 | Ackermann et al. | |
| 9,844,459 B2 | 12/2017 | Badawi | |
| 9,867,988 B2 | 1/2018 | Fink et al. | |
| 9,884,180 B1 | 2/2018 | Ho et al. | |
| 9,895,529 B2 | 2/2018 | Tiedtke | |
| 9,925,373 B2 | 3/2018 | Nirenberg | |
| 9,931,506 B2 | 4/2018 | Chung et al. | |
| 9,937,346 B2 | 4/2018 | Lineaweaver et al. | |
| 9,950,153 B2 | 4/2018 | Wagner et al. | |
| 9,956,425 B2 | 5/2018 | Peyman | |
| 9,962,540 B2 | 5/2018 | Picaud et al. | |
| 9,962,558 B2 | 5/2018 | Peyman | |
| 9,980,388 B2 | 5/2018 | Tai et al. | |
| 9,990,861 B2 | 6/2018 | Chichilnisky et al. | |
| 10,010,364 B2 | 7/2018 | Harrington | |
| 10,071,251 B2 | 9/2018 | Bachinski et al. | |
| 10,112,048 B2 | 10/2018 | Franke et al. | |
| 10,129,647 B2 | 11/2018 | Seo et al. | |
| 10,347,050 B1 | 7/2019 | Wang et al. | |
| 2003/0158588 A1 | 8/2003 | Rizzo et al. | |
| 2003/0199929 A1* | 10/2003 | Snyder | A61N 1/046 607/7 |
| 2003/0233135 A1 | 12/2003 | Yee | |
| 2003/0233137 A1 | 12/2003 | Paul, Jr. | |
| 2004/0106965 A1 | 6/2004 | Chow | |
| 2004/0176820 A1 | 9/2004 | Paul, Jr. | |
| 2005/0004625 A1 | 1/2005 | Chow | |
| 2005/0049578 A1 | 3/2005 | Tu et al. | |
| 2005/0137649 A1 | 6/2005 | Paul, Jr. | |
| 2006/0142818 A1 | 6/2006 | Chow et al. | |
| 2006/0265024 A1* | 11/2006 | Goetz | A61N 1/3706 607/48 |
| 2007/0093877 A1 | 4/2007 | Beecham et al. | |
| 2007/0179564 A1* | 8/2007 | Harold | A61N 1/36046 607/53 |
| 2008/0171929 A1 | 7/2008 | Katims | |
| 2008/0183243 A1* | 7/2008 | Shodo | A61N 1/36046 607/54 |
| 2008/0194531 A1 | 8/2008 | Steer et al. | |
| 2009/0217938 A1 | 9/2009 | Rabe et al. | |
| 2009/0287276 A1 | 11/2009 | Greenberg et al. | |
| 2011/0081333 A1 | 4/2011 | Shantha et al. | |
| 2012/0123501 A1 | 5/2012 | Greenberg et al. | |
| 2012/0296385 A1* | 11/2012 | Gilkerson | G16H 20/40 607/7 |
| 2012/0300953 A1* | 11/2012 | Mauch | H04R 25/554 381/60 |
| 2013/0053733 A1 | 2/2013 | Korb et al. | |
| 2013/0066396 A1* | 3/2013 | Gekeler | A61N 1/36046 607/53 |
| 2013/0184782 A1* | 7/2013 | Eipper | G02C 11/00 607/53 |
| 2013/0274841 A1* | 10/2013 | Eckhous | A61B 18/14 607/101 |
| 2014/0051962 A1* | 2/2014 | Krusor | A61B 5/002 600/386 |
| 2014/0081353 A1* | 3/2014 | Cook | A61N 1/3758 607/59 |
| 2014/0257433 A1 | 9/2014 | Ackermann et al. | |
| 2014/0277435 A1 | 9/2014 | Gefen | |
| 2014/0324147 A1 | 10/2014 | Wagner | |
| 2015/0039067 A1 | 2/2015 | Greenberg et al. | |
| 2015/0157266 A1* | 6/2015 | Machon | A61B 5/6814 600/383 |
| 2015/0209174 A1 | 7/2015 | Abreu | |
| 2016/0051439 A1 | 2/2016 | Brown et al. | |
| 2016/0317474 A1 | 11/2016 | Aung et al. | |
| 2017/0065821 A1* | 3/2017 | Brink | A61N 1/36007 |
| 2017/0266445 A1 | 9/2017 | O'Clock | |
| 2018/0064935 A1 | 3/2018 | Leonhardt et al. | |
| 2018/0078165 A1* | 3/2018 | Machon | A61B 5/291 |
| 2018/0228237 A1 | 8/2018 | Zhang et al. | |
| 2018/0318585 A1 | 11/2018 | Pfeifer | |
| 2018/0318586 A1 | 11/2018 | Salazar | |
| 2019/0091469 A1* | 3/2019 | Gunderson | A61B 5/6869 |
| 2019/0143116 A1* | 5/2019 | Mowery | A61N 1/36034 607/53 |
| 2021/0290952 A1* | 9/2021 | Sunderland | A61N 1/0488 |

FOREIGN PATENT DOCUMENTS

| | | |
|---|---|---|
| EP | 1985332 A1 | 10/2008 |
| GB | 2246709 A | 2/1992 |
| WO | 2006086452 A1 | 8/2006 |
| WO | 2013124141 A1 | 8/2013 |
| WO | 2015095257 A2 | 6/2015 |
| WO | 2016089751 A1 | 6/2016 |
| WO | 2017048731 A1 | 3/2017 |
| WO | 2017064500 A1 | 4/2017 |
| WO | 2018013835 A1 | 1/2018 |
| WO | 2018129351 A1 | 7/2018 |
| WO | 2018208009 A1 | 11/2018 |

OTHER PUBLICATIONS

International Search Report and Written Opinion dated Jul. 10, 2020 for International Application No. PCT/US2020/027438.

Invite to Pay Additional Fees dated Aug. 31, 2020 for International Application No. PCT/US2020/037458.

Chlaihawi et al; "Development of Printed and Flexible Dry ECG Electrodes", Sensing and Bio-Sensing Research, vol. 20, pp. 9-15, 2018.

2019 World Congress Eye and Chip Speaker Abstracts, pp. 20-54, 2019.

Gall et al; Alternating Current Stimulation for Vision Restoration after Optic Nerve Damage: A Randomized Clinical Trial, PLOS One, pp. 1-13, 2016, accessed Nov. 12, 2018.

Chow et al; "The Artificial Silicon Retina in Retinitis Pigmentosa Patients", Trans Am Ophthalmol Soc., vol. 108, pp. 120-154, 2010.

Dawson et al; "Improved Electrode for Electroretinography," Invest. Ophthalmol. Visual Sci. vol. 8, No. 9, pp. 988-991, Sep. 1979, accessed on May 2, 2019.

Diagnosys DTL Brochure, Diagnosys, LLC, 2016, Accessed Nov. 20, 2017.

DTL Installation, Diagnosys LLC, Accessed Oct. 6, 2020.

Bittner et al; "Longevity of Visual Improvements following Transcorneal Electrical Stimulation and Efficacy of Retreatment in Three Individuals with Retinitis Pigmentosa", Graefe's Archive for Clinical and Experimental Ophthalmology, 2017, Published online on Dec. 8, 2017.

H110002B Summary of Safety and Probable Benefits, Second Sight Medical Products Inc., issued Dec. 11, 2001.

H110002C Second Sight Manuals, Second Sight Medical Products Inc., 2013.

Naycheva et al; Phosphene Thresholds Elicited by Trasncomeal Electrical Stimulation in Healthy Subjects and Patients with Retinal Disease, Investigative Ophthamology and Visual Science, vol. 53, No. 12, pp. 7440-7448, 2012, accessed on Sep. 20, 2018.

Schaiz et al; "Transcorneal Electrical Stimulation for Patients with Retinitis Pigmentosa: A Prospective Randomized, Sham-Controlled Follow-Up Study Over 1 Year", Investigative Ophthalmology and Visual Science, vol. 58, No. 1, pp. 257-269, 2017. Accessed on Sep. 25, 2018.

Scyfix SF700 Manual, Instructions for Use, pp. 1-28, Scyfix LLC.

Stauffer et al; "Skin Conformal Polymer Electrodes for Clinical ECG and EEG Recordings," Advanced Healthcare Materials pp. 1-10, 2018.

Manthey et al; "Using Electrical Stimulation to Enhance the Efficacy of Cell Transplantation Therapies for Neurodegenerative Retinal Diseases: Concepts, Challenges, and Future Perspectives", Cell Transplantation, vol. 26, pp. 949-965, 2017.

(56) References Cited

OTHER PUBLICATIONS

Invitation to Pay Additional Fees dated Dec. 17, 2019 for International Application No. PCT/US2019/054028.

* cited by examiner

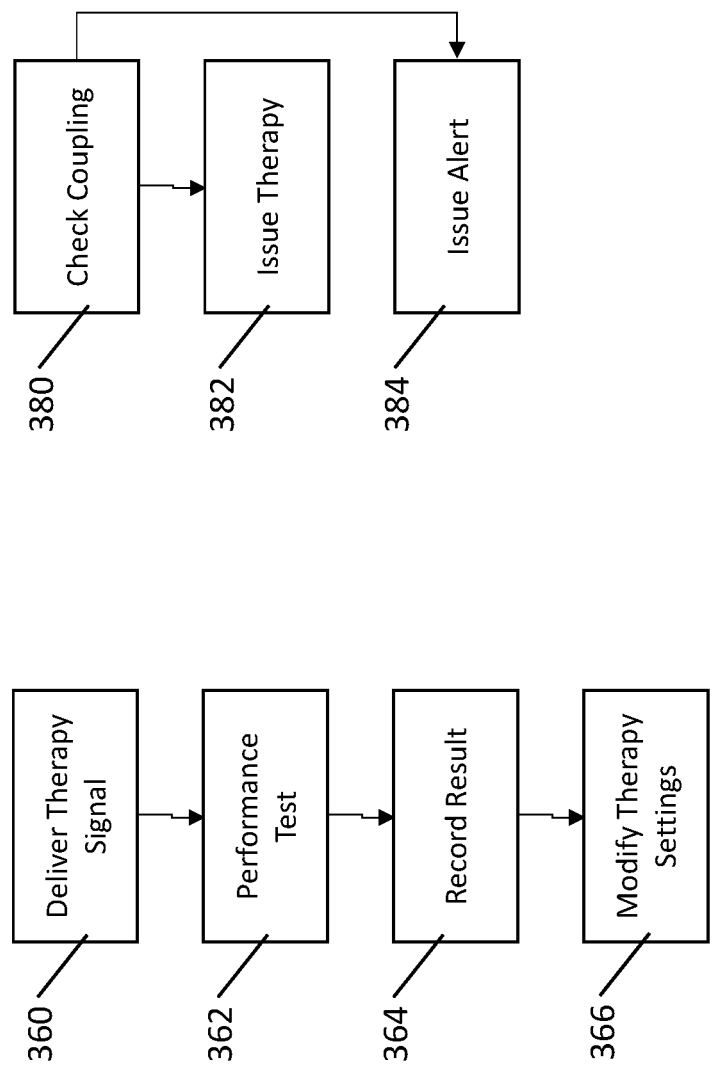

SYSTEM AND METHODS FOR CONTROLLED ELECTRICAL MODULATION FOR VISION THERAPY

CROSS REFERENCE TO RELATED APPLICATIONS

The present application claims the benefit of and priority to U.S. Prov. Pat. App. No. 62/739,810, filed Oct. 1, 2018, the disclosure of which is incorporated herein by reference.

FIELD

The present invention relates generally to the field of ophthalmic treatments for diseases of the eye. More particularly, the present invention is directed to systems and methods adapted to provide stimulus, such as by electrical stimuli, to the eye.

BACKGROUND

Therapy to prevent or reverse diseases of the eye is of great interest. As life expectancy expands, more and more of the population is at risk for age related macular degeneration (AMD). Meanwhile, smaller populations of young patients suffer from a variety of genetic diseases, including Stargardt's disease, that affect the retina of the eye. A wide variety of other vision disorders exist which can lead to partial or total blindness.

SUMMARY

There is a continuing demand for new and alternative systems and methods to treat such disorders including by preventing, arresting or reversing disease progress, or at least by alleviating ongoing symptoms. In some examples, such systems may be aided by the inclusion of additional apparatuses, features and/or routines for determining whether therapy is effectively reaching its target. In some examples, verification of therapy is performed by monitoring patient characteristics during therapy delivery. In some examples, verification of therapy is achieved by having the patient perform tests before, during, and/or after therapy delivery.

The above summary of some embodiments, aspects, and/or examples is not intended to describe each embodiment or every implementation of the present disclosure. The figures and the detailed description which follows more particularly exemplify these embodiments.

BRIEF DESCRIPTION OF THE FIGURES

The disclosure may be more completely understood in consideration of the following detailed description of various embodiments in connection with the accompanying drawings, in which:

FIGS. 7-9 are flow diagrams for illustrative examples.

Figure 1:
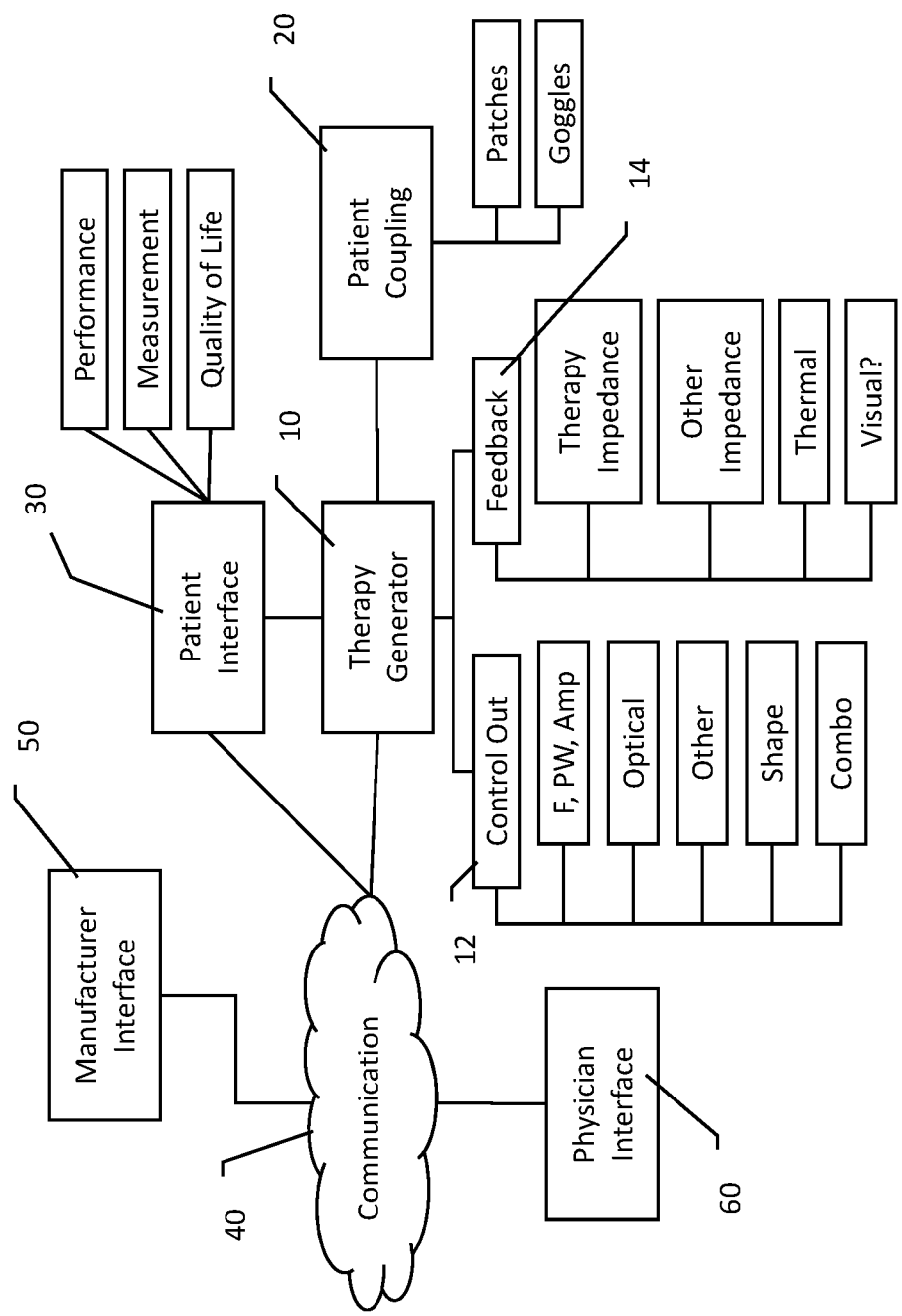
FIG. 1 illustrates a therapy system using functional blocks.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

In some examples, new systems and methods for monitoring ocular modulation therapy as it is applied are disclosed. As used herein, ocular modulation refers to the treatment of the eye with a signal, delivered invasively, non-invasively, or minimally-invasively, to achieve a therapeutic benefit. Therapeutic benefit may include, for example and without limitation, improving or altering blood flow, upregulating or downregulating synthesis, degradation, binding, release or activity of proteins, enzymes, DNA, RNA, polysaccharides or other endogenous physiological or pathological biomolecules; and/or upregulating, downregulating, activating, deactivating physiological or pathological biopathways, etc. Ocular modulation may be combined with the administration of pharmaceuticals, exogenously derived biomolecules, cell therapy, or photo-, electro- or magneto-reactive or active particles, such as nanoparticles, before, during or after an electrical signal is applied.

In some examples, the devices and systems disclosed herein are suited for use in conjunction with exogenous and/or endogenous stem cell transplantation therapies. For example, a method may comprise delivery of electrical stimulation before, during, or after stem cell transplantation to improve cell survival, repair and/or replacement. In illustrations, the use of methods and systems disclosed herein may enhance native cell survival, transplanted cell survival, transplanted cell integration, and functional synapse formation and/or axon regeneration. Non-limiting examples of endogenous stem cell types which may be suitable for transplantation in combination with systems or devices of the present invention include Müller cells, retinal pigment epithelial cells (RPE cells) and ciliary pigmented epithelial cells (CPE). Non-limiting examples of exogenous stem cells suitable for transplantation according to some embodiments of the invention include neural stem cells (NSCs), mesenchymal stem cells (MSCs) derived from bone marrow, adipose tissue or dental pulp and stem cells from the inner cell mass of the blastocyst and induced pluripotent stem cells (iPSCs). See, for example, "Using Electrical Stimulation to Enhance the Efficacy of Cell Transplantation Therapies for Neurodegenerative Retinal Diseases: Concepts, Challenges, and Future Perspectives", Abby Leigh Manthey, et al., Cell Transplantation, Vol. 26, pp. 949-965, 2017.

In some examples, combination of therapy systems of the invention with biological or pharmaceutical agents may provide improved efficacy or reduced side effects associated with such biological or pharmaceutical agents when administered alone. Pharmaceutical agents currently used to reduce the growth of new blood vessels in wet AMD include anti-angiogenics such Bevacizumab (Avastin®), Ranibizumab (Lucentis®) and Aflibercept (Eylea®), etc. While the benefit of these agents for mitigating symptoms associated with wet AMD are well-known, these agents also may have side effects including increased eye pressure, inflammation of the eye and others. A benefit of systems disclosed herein includes modulation of cytokines and other endogenous inflammatory factors involved in the inflammation process.

In some embodiments it is foreseen that administration of anti-angiogenic agents listed above or other pharmaceuticals in combination with electrical therapy applied simultaneously with, before (e.g. 1, 2, 12, 24, 36, 48 and/or 96 or more hours before), or after (e.g. 1, 2, 12, 24, 36, 48 and/or 96 or more hours after), injection of such anti-angiogenics, at stimulation parameters used herein, may beneficially improve the efficacy and/or reduce the likelihood of side effects associated with administration of such agents.

Several different modes of energy delivery can be used including mechanical delivery (such as sonic energy, including for example, ultrasound), light-based delivery (such as by the delivery of collimated or non-collimated light of selected wavelengths, for example using a laser, a light emitting diode, etc.), electrical delivery (such as by the delivery of an electrical signal), and/or magnetic delivery (such as by generating a magnetic field or fields). In some examples, one mode of therapy delivery is used, while the same or a different mode is used to monitor therapy delivery. One component of several examples is the use of configurations that are adapted to provide enhanced tissue contact, enhanced therapy delivery, improved efficiency of energy delivery, targeted therapy locations, improved user comfort and/or compliance, and/or reduced likelihood of tissue injury or irritation.

In an illustrative example, a system includes output circuitry for delivering electrical stimuli to the eye of a patient. The output circuitry may include one or more output channels, operable independently to provide greater control over current output than is possible with a single output channel. By controlling output across more channels, the resultant field can be controlled in a manner that allows the physician to tailor therapy to the particular patient's anatomy. For example, when the target for therapy is in the back of the eye, shaping the developed field to ensure coverage of the therapeutic target can be better facilitated with a plurality of output channels. 2, 3, 4 or more channels for output currents may be provided. Other examples may have a single channel output.

In another illustrative example, impedance encountered by one or more electrodes may be monitored to ensure efficacy and safety. For example, where a pair (or more) electrodes are on a patient, a signal passing between the electrodes provides information about the impedance and hence contact/coupling of the electrodes to the patient, such as by delivering a controlled voltage and monitoring output current, or by delivering a controlled current and monitoring output voltage. In another example, if a patient is equipped with a three electrode system, having a pair or more output electrodes, and one or more indifferent electrodes, impedance encountered by the signal passing between the output electrodes can be monitored, while the electric field incurred at the indifferent electrodes may be measured as well, providing a larger picture of electrode contact conditions including both active and inactive electrode interfaces. In an example, two output electrodes may be, for example, an electrode patch for each of the left and right eyes. Alternatively, two patches may be used for one eye such as by having a medial and lateral patch located on either side of the eye, or superior and inferior patch located above and below one eye. A single patch may be provided with multiple contacts or electrodes, if desired, and, in some examples, the multiple contacts on a patch may be selectable. The indifferent electrode may be placed away from the eye, such as behind the ear, on the back of the head, on the back of the neck, on the shoulder, or on the patient's limb such as on the hand, arm, leg or foot.

For example, to perform impedance monitoring, a low amplitude signal may be used, having features that will not stimulate the patient, such as using a short pulse width or low amplitude well below a stimulus threshold, may be issued and monitored to avoid stimulus during the test. In other examples, impedance can be monitored using therapy-level signals. By such an approach, the system may determine whether the patient has properly placed each of the output electrodes and/or determine whether one of the output electrodes has come loose or is improperly positioned or located during a therapy session. Impedance can serve to indicate safety as, for example, if the patient has not placed an electrode well, the area of contact with the skin or other tissue may be reduced, increasing current density and potentially leading to burns. A very low impedance may indicate that, for example, when a conductive patch, such as a gel patch, is being used, the metal wire that is typically covered by the patch has become exposed directly to the tissue, which can again lead to irritation or burns. Impedance may also be used to determine whether therapy signals that have been delivered are in fact getting to the desired target tissue. For example, delivering a voltage signal when impedance is above a desired range may lead to ineffective therapy.

In another example, tissue impedance variation at the site of the electrode contact with the patient due to tissue hydration status or surface/contact moisture conditions can be measured. In some examples, adjustment of therapy delivery parameters can be made based on impedance testing to ensure consistent therapeutic delivery parameters are delivered to the eye.

Impedance monitoring can also be used to observe whether there are any changes to the patient anatomy during therapy delivery. For example, with various visual system diseases, the diseased or inflamed retinal cells eventually lose cell function, raising impedance at those cells, while causing other changes such as a drop in protein synthesis, reduced adenosine triphosphate levels, etc., eventually leading to cell death. Again returning to an example with two output electrodes and one indifferent electrode, impedance may be measured to inspect for changes in the impedance within the eye. Rather than passing current from one of the output electrodes to a remotely placed indifferent electrode (such as on the neck, torso or a limb), which will incorporate a large amount of tissue making the measurement potentially very noisy and subject to patient changes such as posture and hydration, a signal for monitoring therapy efficacy may be delivered from one output electrode to the other. In another example, with multi-contact output electrodes, the signal used to measure therapy progress may pass between two contacts on the same output electrode, making for a more local measurement.

In some examples, additional monitoring methods are used. In one example, a patient is provided with a visual interrogation apparatus, or may use a personal device such as a smartphone camera for visual interrogation. A photograph of the eye of the patient, during therapy and/or with or without visual stimulus, can be used to image the retina of the patient. By taking a photograph before a therapy session, and again after the therapy session, and comparing the two photos, the effect of therapy on the eye may be determined, giving useful data about the efficacy of the therapy session. Comparison may also be had to photos taken earlier in time, such as before any therapy was even prescribed or instructed. The "after" photo may be taken immediately after therapy session completion, or may be after some period of time, whether minutes, hours, days and/or weeks or months, have passed. It may be that a series of photos, such as photos taken within hours of treatment, and photos taken after weeks of treatment, or photos taken months after treatment, may be useful to determine disease progress.

As used herein, a therapy session should be understood as the performance, by a patient, of a therapy regimen. Typically the therapy regimen will be prescribed or instructed by a physician. An example therapy regimen may be to apply cutaneous patch electrodes, couple the electrodes to a pulse generator, and activate the pulse generator while wearing the electrodes for a period of time. The pulse generator may use various tools to monitor the duration that therapy is delivered, and whether good contact of the electrodes to patient skin is maintained during therapy, in order to confirm that the prescribed or instructed regimen was followed.

In some examples, therapy is delivered using a duty cycle, such as by delivering an output stimulus for a defined period of time, with stimulus "off" for a period of time. The duty cycle is defined as a percentage, by dividing the total time that therapy is on during a session by the total duration of the session, or may be determined for shorter intervals such as relative to a segment of the total therapy session. During "off" times, the described impedance measuring may take place, for example, to monitor contact as well as therapy progress or parameters. Impedance may be measured during stimulus delivery as well, if desired.

In another example, the patient may be prompted to engage in performance testing. For example, an application on a smartphone, or a screen provided in association with a pulse generator, may present images to the patient to test visual acuity or contrast sensitivity before, during and/or after a therapy session. In another example, the patient may be prompted to answer questions regarding the therapy session experience, and/or questions about patient status and behavior. For example, questions may request subjective input as to whether the patient is feeling well, anxious, tired, or wide awake, whether the patient believes himself or herself to be dehydrated, well hydrated, hungry, or sated, or whether the patient has consumed any medication, drug, or other substance that could affect therapy. Information regarding patient visual acuity status using traditional vision tests or modifications thereof suitable for administration from a personal device (such as a tablet computer or smartphone) or the therapy device may be provided. Tests may include, for example, a Snellen test, a random E test, a kinetic field test, a Goldmann test, an Amsler test, a Humphrey test, or other tests for contrast, visual acuity, visual field, tracking, color, brightness, peripheral field. Quality of life questions may also be provided by the patient interface, such as determining whether the patient feels he or she is seeing better, or whether the patient is engaging in more, less or different activities than previously. The information can be stored for future analysis or correlation with other information, or immediately correlated with other information provided including therapy delivery parameters. Such information may be communicated from the patient device (whether a smartphone, a dedicated controller or patient interface, or the therapy generator) to physician or manufacturer systems as desired.

In other examples information may include patient entered responses to electrically evoked phosphene thresholds (EPT) that may be correlated with electrical stimulation parameters, visual acuity, patient disease status or other information about the patient or the therapy. Furthermore, data on particular patterns or morphology (snow flakes, stars, lightening bolts) of the evoked phosphenes may be recorded. Information may also be collected from physician administered testing including Early Treatment Diabetic Retinopathy Study Charts (ETDRS Visual Acuity Tester), slit lamp biomicroscopy, fundus examination, tonometry, static and kinetic perimetries, electroretinogram (ERG) readings, electrooculography (EOG) readings for measuring the corneo-retinal standing potential that exists between the front and the back of the human eye, optical coherence tomograph (OCT) readings, flicker testing, etc. Such information may be obtained from the patient, through testing or query, and stored, conveyed, or analyzed for correlations, whether immediately or later, by the patient, physician, or manufacturer systems.

In some examples, new systems and methods are disclosed for providing the physician greater access to status and therapy history for a patient. As just indicated, various data may be gathered by the system before, during, and after a therapy session. The data may include impedance or other measurements, as well as image data, and therapy session data itself such as what stimulus amplitudes (or other variables or parameters) were applied, and for how long. In some examples, the pulse generator may be equipped with communications circuitry, such as cellular, WiFi or Bluetooth™ drivers and antennae, to transmit session data or any data related to other images and measurements to a remote server or directly to the physician. In an example, the pulse generator communicates to a patient's computer, tablet, or smartphone, which may have an app on it to communicate received data to a server or the physician. A physician may be notified when new information is available, if desired. In some examples, a physician may be able to access therapy session and other information that has been transmitted by the patient device (whether pulse generator or cell phone) when convenient, or when the patient visits the physician for a follow-up.

The therapy output in some examples is of sufficiently low voltage and/or current to allow a patient's device, such as a smartphone, tablet or computer, to serve as the pulse generator. For example, currents may be 10 milliamps or less, and more typically 5 milliamps or less, with voltages under 32 volts (which may require a step-up voltage circuit) or under lesser voltages, such as under 5 volts, using frequencies and pulse widths as described below. In one example, a standard connector, such as a USB Port or speaker port (or company specific proprietary connector), may be used as a power source and communications link for a pulse generator, which can simply plug into a patient device to receive power and control signals, and also to provide feedback signals such as sensed impedance. For example, an output of less than one volt, or less than one milliamp of controlled current, may be provided, with a pulse rate in the range of 0.05 Hertz up to as much as 20,000 Hertz, or 0.1 Hertz up to 1,000 Hertz. In some examples, the pulse rate may be up to 300 Hz, or in the range of 10 to 30 Hz.

Outputs may be in the range of 100 nanoamps, or 100 nanowatts, or 100 nanovolts, or lower, if desired, up to the range of microamps, microwatts, or microvolts, or up to the range of milliamps, milliwatts, or millivolts, or higher. In some examples, the impedance encountered may call for voltage or power to exceed 1 volt and/or 1 watt, though current in many cases will remain below 1 amp. In an example, the maximum current may be 10 milliamps. In some examples, voltage may be as high as 1 volt, or as high as 50 volts. The duty cycle of any therapy output may be controlled as well, for example, between 10% to 100% duty cycle may be use.

Pulse widths of as short as a few nanoseconds, for example as short as 10 nanoseconds, up to 1 second, or more or less, may be used; in some examples, the pulse width is defined in a microsecond range, for example, between 10 and 100 microseconds. In other examples, a millisecond level pulse width may be used, such as between 1 and 100 milliseconds, for example, 10 milliseconds, delivered at 10 to 30 Hz.

Charge balance may be maintained on the tissue interface electrodes by, for example, using a biphasic waveform, or by using a monophasic waveform and switching polarity occasionally or periodically. A sequence of therapy may be delivered with one or more of frequency, amplitude, pulse width, waveform type (i.e. monophasic or biphasic, current controlled or voltage controlled, etc.) changing within different parts of a session. The output waveform may be tailored to a range of expected impedances such as between 10 ohms and 1 gigaohm, or 500 ohms to 10 megaohms, or 1 to 100 kilohms, for example. In some examples, the output waveform may be defined in part by a maximum charge per pulse, for example, less than a set quantity of coulombs (such as less than 500 nC at a load of 500 ohms, for example).

Some examples comprise a physician interface device that can be used to program a pulse generator which the patient can then take home. The programming provided by the physician may define the therapy regimen by setting parameters for stimulus delivery.

If desired the patient may be allowed to modify one or more stimulus delivery parameters, such as by raising or lowering the amplitude of stimulus.

In various examples, the condition to be treated may include one or more of the following: macular degeneration, inherited retinal disease, presbyopia, diabetic retinopathy, and glaucoma. In further embodiments, the condition to be treated may include one or more of the following: retinitis pigmentosa, Stargardt's, CMV-retinitis, Best's disease, macular dystrophy, optic neuritis, ischemic anterior optic neuritis, Usher's syndrome, Leber's congenital amaurosis, cone-rod dystrophy, cone dystrophy, choroideremia and gyrate atrophy, central retinal artery occlusion, central retinal vein occlusion, branch retinal artery occlusion, branch retinal vein occlusion, central serous chorioretinopathy, cystoid macular edema, ocular histomplasmosis, ocular toxoplasmosis, retinopathy of prematurity, amblyopia, strabismus, nystagmus, cataracts, refractive errors, and/or corneal conditions including corneal lesions and abrasions including surgical wounds, as well as dry eye, conditions amenable to nerve stimulation including by stimulation of the facial nerve, and any other ophthalmic, eye, or vision-related condition, disease, disorder, abnormality or damage.

In some examples, the mechanism of operation may comprise the application of transocular electrical and/or light-based stimulus to modify transmembrane potentials of cells or within cells, to modify ion and molecule levels or distributions, to modify (such as increasing or reducing) alkalinity in desired spatial locations, to modify (such as by increasing or decreasing) the production of select chemicals (such as hydrochloric acid), to cause motive effects on ions or molecules such as by attracting oxygen to the treated region, to cause vasorelaxation or vasoconstriction, to reduce or arrest local hemorrhage, to sedate, to increase tonicity of local tissues, to counteract sepsis, to produce fibroplasia, or to reduce neuromuscular spasticity or irritability. Such stimulus may act on cells which have become dormant, without yet suffering cellular death, in the stimulated region, potentially acting to delay or even reverse the disease process, triggering an increase in adenosine triphosphate levels and/or increasing or initiating protein synthesis; triggering increases or changes in neurotropic agents such as ciliary neurotrophic factor (CTNF) and/or brain-derived neurotrophic factor (BDNF); growth factors such as insulin growth factor-1 (IGF-1), fibroblast growth factor-2 (FGF-2); immune mediators including cytokines; neuroprotective genes such as B-cell lymphoma-2 (BCL-2), BAX, or tumor necrosis factor genes; or other cellular products. Another example may take the form of a method of stimulating a Müller cell to upregulate neurotrophic factors, to downregulate inflammatory factors, or to support new cell growth, such as may occur if electrical or other stimulation is used to induce a subset of neural progenitor or stem cells to regenerate photoreceptors and/or neurons in and around the eye.

FIG. 1 shows an illustrative system. The illustrative system includes a therapy generator 10, which is electrically (and/or, optionally, optically) connected to a patient coupling apparatus 20 for delivering stimulus to a patient. The therapy generator 10 may include or be connected or connectable to a patient interface 30, to allow the patient to control and/or deliver feedback to the therapy generator 10.

The therapy generator may include input and output circuitry, which may be combined into a single unit, or may be provided as separate circuit elements, including a control out 12 that can generate and deliver stimulus to the patient via the patient coupling 20. The control out 12 may provide stimulus in an electrical form, for example, with control over frequency, pulse width and/or amplitude, for example, as well as inter-pulse delay, patterning, and any other suitable feature. In an example, the output is delivered in electrical form with delivery of a series of pulses, such as square waves (though other shapes, such as a sinusoid, may be used). Output electrical stimulus may be delivered using one or more channels for therapy output in one or more of voltage controlled or current controlled form.

In an illustrative example, the output stimulus takes the form of a series of square waves delivered at a relatively higher frequency (1 kHz to 100 kHz, for example), modulated at a lower frequency (1 Hz to 1 kHz), in which the lower frequency for modulation is varied over time. The square waves may be biphasic, or they may be monophasic with periodic polarity switching. In an example, a 10 kHz square wave of a pulse width 48 microseconds is a carrier, and is modulated at different frequencies (about 0.3 to about 300 Hz) for different durations within a therapy session, such as described in U.S. Pat. No. 7,251,528, the disclosure of which is incorporated herein by reference. Rather than a square wave, a sinusoid or other shape may be used. In another example, the carrier wave may be varied within a range of 10-30 Hz.

In another example, a square wave or sinusoidal wave, or other wave shape, is delivered using a 10 milliseconds, biphasic waveform (5 milliseconds positive phase, 5 milliseconds negative phase), with the biphasic waveform called at a frequency in the range of about 0-300 Hz, or 0.3-0.5 to 300 Hz, or in a range of about 10-30 Hz, or at a frequency of 20 Hz.

In some examples, optical output, such as a light output generated by a laser (such as using a vertical cavity surface emitting laser, light emitting diode, or any other suitable optical output generating device, may be provided. Again, the wavelength of such output can be controlled or selectable, as by using a pulsed or shuttered output at a selected frequency, if desired. Other outputs, such as a sonic or magnetic field output may be provided in some examples. Sonic output may be generated by providing a transducer in the therapy generator 10 or by powering a transducer in a patient coupling apparatus. Magnetic field output may be generated by providing an electrical signal to an inductor provided in the vicinity of the targeted tissue, such as using inductors placed in the patient coupling. Any of these stimulus modalities may be combined in patterns for sequential output or may be delivered simultaneously, as desired.

The therapy generator 10 and patient interface 30 may be provided in a single unit, such as a custom hardware or via a smartphone. In some examples, therapy generator 10 is provided as an add-on to an off the shelf patient interface 30, such as by having the therapy generator coupled to a smartphone using a wire or cord that couples to a plug (such as a USB, mini-USB, or headphone port). In an example, the therapy generator 10 is a separate hardware element having its own power supply and including a communication module, such as an RF, WiFi, or Bluetooth™ communications module to communicate with the patient interface 30. Some examples may use a therapy generator 10 that is wearable by the patient, such as in a head worn apparatus (a headband, hat, glasses frame, eyepiece, goggles, partial facemask, or earpiece, for example), a neck worn apparatus, or an apparatus that may be worn on a cuff on a limb, or held by a harness on the torso, as variously disclosed in U.S. Prov. Pat. Apps. 62/774,093, filed 30 Nov. 2018 and titled HEAD WORN APPARATUSES FOR VISION THERAPY, 62/832,134, filed 10 Apr. 2019 and titled SYSTEMS AND INTERFACES FOR OCULAR THERAPY, 62/861,658, filed 14 Jun. 2019, titled WEARABLE MEDICAL DEVICE, 62/867,421, filed 27 Jun. 2019 and titled SYSTEMS AND INTERFACES FOR OCULAR THERAPY, 62/873,450, filed 12 Jul. 2019 and titled OCULAR THERAPY MODES AND SYSTEMS, and/or 62/884,890, filed 9 Aug. 2019, titled WEARABLE MEDICAL DEVICE, the disclosures of which are incorporated herein by reference. The therapy generator 10 may additionally or alternatively comprise circuitry and functionality, at least in part, as disclosed in U.S. Pat. No. 7,251,528, titled TREATMENT OF VISION DISORDERS USING ELECTRICAL LIGHT AND/OR SOUND ENERGY, the disclosure of which is incorporated herein by reference.

The patient coupling 20 may include a wearable apparatus such using patches or goggles that the patient can wear on the skin. In some examples, one or more patches are worn or applied near the eye. If desired, an electrode may be placed under the skin, directly on the skin, on the eyelid, or beneath the eyelid. An electrode may, if desired, be placed in the sinus cavity or elsewhere on the patient. In general, the patient coupling 20 will typically be non-invasive, that is, without breaching the skin of the patient. A wearable contact lens may be used, if desired. A return electrode or indifferent electrode may be placed elsewhere on the patient such as on the back of the neck, at the base of the skull, on the shoulder, arm, hand, or chest of the patient. Patient couplings may include electrodes disposed near or at the eye/eyelid on wearable patches for skin contact, electrodes (which may be wettable) that contact the tissue surrounding the eye including the canthus and/or conjunctiva, wearable frames, partial facemasks, goggles, as well as remote electrodes elsewhere on the head or on the neck, torso, limb or extremity of the patient, as well as internal to the patient such as in the sinus cavity. A variety of illustrative electrode positions and apparatuses to hold electrodes in desired positions are disclosed in U.S. Prov. Pat. Apps. 62/774,093, 62/832,134, 62/861,658, 62/867,421, 62/873,450, and/or 62/884,890, as well as U.S. Pat. No. 7,251,528, the disclosures of which are incorporated herein by reference.

The patient interface 30 may include, for example, one or more buttons or other controls, a speaker and/or microphone, a screen, a touchscreen, or any other suitable interface for communication with a patient to facilitate patient control over the therapy generator. For example, the patient may turn therapy on or off, or may be allowed to control stimulus output by modifying a selected type of stimulus output, or by changing amplitude of output to ensure comfort and observable efficacy. For example, a patient may be able to directly observe whether an electrical therapy is having an effect by determining whether phosphenes (a phenomenon whereby the patient can observe a ring or spot of light produced by pressure on the eyeball or direct stimulation of the visual system other than by light) appear when therapy is on. In some examples, the generation of phosphenes is desirable during therapy, and so the patient may be encouraged to adjust amplitude (such as by raising it) until phosphenes are observed. In other examples, the presence of phosphenes may be deemed to indicate that amplitude is above a desired level, and the patient may provide feedback to indicate that phosphenes are observed and therapy amplitude or other control of energy output may be reduced. User interface designs, functionality and concepts may also be as disclosed in U.S. Prov. Pat. Apps. 62/774,093, 62/832,134, 62/861,658, 62/867,421, 62/873,450, and/or 62/884,890, as well as U.S. Pat. No. 7,251,528, the disclosures of which are incorporated herein by reference.

For example, a combination therapy may comprise an electrical stimulus delivered at a level that is below that required to generate phosphenes electrically, while an output of a sonic nature may be used to generate pressure in the eyeball to cause a phosphene to be observed. If desired, the sonic output would be used to confirm appropriate contact between the patient coupling and the target tissue.

In addition to using the patient interface to obtain data during therapy to indicate that the therapy is being received, the patient interface may be used before, after, or intermediate to therapy sessions to observe patient status such as by using visual tests to determine if there are changes in patient visual capabilities. Queries or tests may be generated by the patient interface to determine how the patient performs in certain tests, to measure patient behavior or skills, or to obtain quality of life observations from the patient.

In some examples, the therapy generator may also obtain feedback as indicated at 14 using the patient coupling. For example, the impedance during or between stimulus outputs may be observed such as by sampling such impedance(s). Thermal feedback may also be obtained, as well as visual feedback as by, for example, generating an optical output to be delivered into the eye and observing characteristics of the reflected signal. Such feedback 14 may be obtained for the purposes of, but is not limited to, determining whether the patient coupling 20 is adequate (for example, whether goggles or patches are correctly placed or worn) or to determine any immediate changes to patient physiology (such as a change in patient impedance). In an example, patient coupling impedance may be sampled between stimulus outputs using a lower amplitude or pulse width output to confirm coupling efficiency, while patient physiology may be measured during stimulus outputs; the coupling impedance may be local such as by having two electrodes on the same patch and determining impedance between the two relatively closely spaced electrodes, while the stimulus impedance may be more global by measuring impedance between a first patch and a second patch or an indifferent electrode placed remotely from the targeted tissue. Such feedback may be used within a therapy session to alert the patient to a lack of proper contact or placement of the patient coupling, and/or to track longer term usage and/or progress.

One or more of the therapy generator 10 or patient interface 30 may include Bluetooth™, cellular or WiFi circuitry for communicating by a communication intermediary 40 to a manufacturer interface and/or physician interface. The communication intermediary may be the Internet, for example, though in other examples, communication intermediary may simply be a medium, such as air, through which communication signals are sent as would be the case with Bluetooth™ and various other RF technologies. Infrared or other communication modalities may be used as desired. The manufacturer interface 50 and physician interface 60 may be used to obtain various metrics regarding the use and efficacy of the therapy generator. For example, patient interface tests and feedback may be obtained, as well as records of amplitudes or other patient controlled (to the extent such control is allowed) characteristics of the delivered therapy. Duration and frequency of therapy sessions may be observed. Information in the manufacturer interface for one patient may be placed in a database to allow observation across a population, potentially allowing for later comparison of patient outcomes to patient usage to optimize therapy regimens. The physician interface 60 may be useful to the physician to better manage a given patient's usage and determine if the patient is responding to therapy. For example, a patient who does not respond to therapy may not respond due to the patient's unique physiology, while another patient may not respond simply because the device is not being used correctly (poor patient coupling usage, misplacement, or broken product), or therapy not being used enough, or other patients may require that the applied therapy be changed, for example, to a wider or narrower pulse width, a higher or lower frequency, a different wave type (sinusoid instead of square, or current controlled instead of voltage controlled), or with different amplitude.

In some examples the physician interface 60 may be used to manage what therapy outputs the therapy generator can provide, as well as to determine how much control, if any, the patient can have over the therapy.

In some examples, the system may be designed to continuously self-optimize by collecting, interrogating and acting upon identified learnings from patient and product interaction and information. Functional connectivity of the therapy generator and/or patient interface 30 to the physician interface 60 may provide for ease of use and reliability to drive patient satisfaction and compliance. Digital connectivity may provide communication and information collection. Communication in the example shown may include patient-to-doctor, doctor-device and/or patient-device communication. Real time and/or continuous communication and data collection combined with robust patient compliance may enhance the likelihood and extent of successful outcomes for individual patients and across the patient population.

Figure 2:
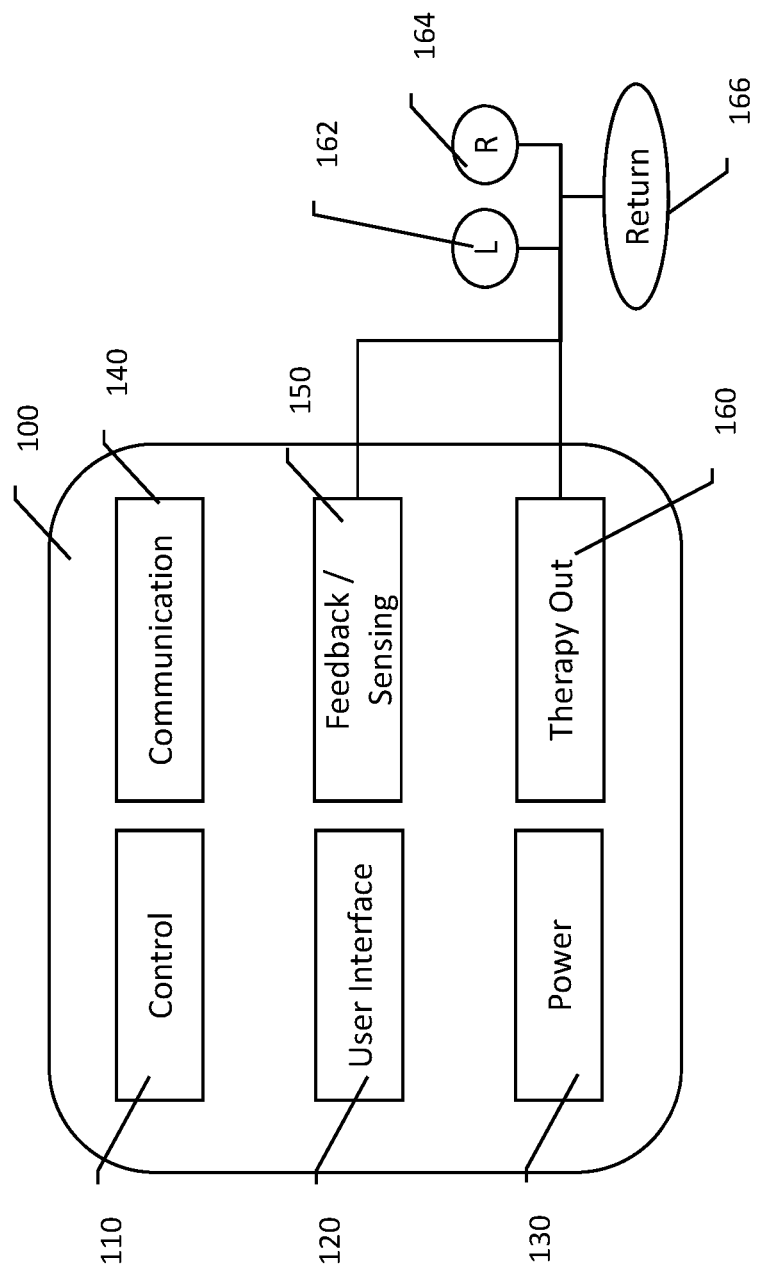
FIG. 2 shows schematically another therapy system using functional blocks.

FIG. 2 shows another illustrative example. Here a patient therapy generator is shown at 100. In this example, a control circuitry 110, such as a microcontroller, microprocessor, or state machine, for example and without limitation, is provided. The device 100 may also include communication circuitry 140 (such as RF, Bluetooth™ infrared, WiFi, cellular, or other communication). A user interface 120, such as buttons, a microphone and/or speaker, screen, touchscreen, keyboard, or other user interface, is also provided. Therapy output 160 and feedback modules 150 are illustratively shown; such modules may be in the form of dedicated circuitry or may be integrated into the controller. Power 130 may be provided by, for example, replaceable or rechargeable batteries and/or plug-in-type power. At least the therapy output 160 and feedback sensing module 150 are configured to be coupled to one or more patient coupling devices, illustratively shown as electrode patches for left and right eyes 162, 164, along with an indifferent or return electrode 166. Sampling circuitry, as well as filtering and/or amplification circuitry may be part of the feedback/sensing module 150, including for example, analog to digital conversion circuits. Current or voltage generating, buffering and amplifying circuits, as well as voltage step-up circuitry, may be included in the therapy output circuitry 160, to allow electrical energy taken from the power circuit 130 to be delivered in suitable therapy format to the electrodes 162, 164, 166. Additional designs and circuitry for control circuitry 110, user interface 120, power 130, communication 140, feedback module 150, and therapy output 160 are disclosed in U.S. Prov. Pat. Apps. 62/774,093, 62/832,134, 62/861,658, 62/867,421, 62/873,450, and/or 62/884,890, as well as U.S. Pat. No. 7,251,528, the disclosures of which are incorporated herein by reference.

In some examples, the features of a user interface may provide an interactive experience to the patient by, for example, providing or receiving voice commands to and from the user. The system may comprise computer readable media, which may be non-transitory, to store executable instruction sets including voice recognition and/or voice emulation/generation capabilities, in one or several languages, to add to ease of use. It may be noted, for example, that the likely patient for such systems may already be visually impaired, such that the use of voice commands and activation may be particularly helpful in some examples. In further examples the user interface may be additionally tailored to low vision or blind patients by providing text narration, texture or tactile-based features, braille text and using human factors approaches to aid the user.

It is envisioned that therapy sessions may be performed, for example, weekly, daily, or twice daily, or at other intervals, as desired, and may last for several minutes, such as up to 30 minutes or more. During therapy, the pulse generator 100 may also be adapted to provide the user with other functionality, such as audio output to listen to music or use a cellular telephone, if desired.

Figure 3:
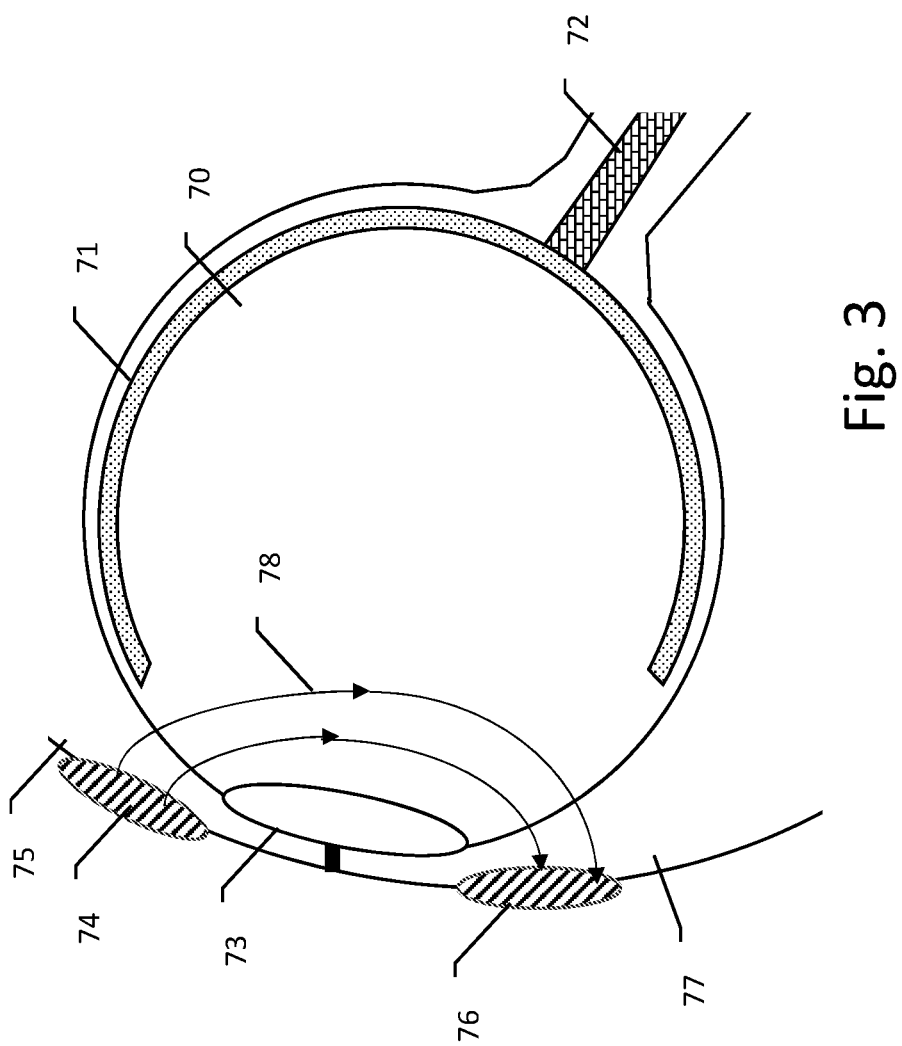
FIG. 3-4 illustrates eyes receiving electrical therapy in different forms.

FIG. 3 illustrates a bipolar approach to electrical stimulation of the eye. The patient's eye is shown at 70, with the retina generally at 71 and the optic nerve at 72. The cornea is represented at 73. A first electrode 74 is shown on the upper eyelid 75 of the patient, and a second electrode 76 is shown on the lower eyelid 77 of the patient. Electric field lines 78 show the electric field that may be induced by delivering a therapy pulse between the electrodes 74, 76. The impedance between the electrodes will be low in this example, as the electrodes 74, 76 have relatively close spacing. As can be seen, the current flow and induced fields tend to be more focused toward the front of the eye when using a bipolar approach.

Figure 4:
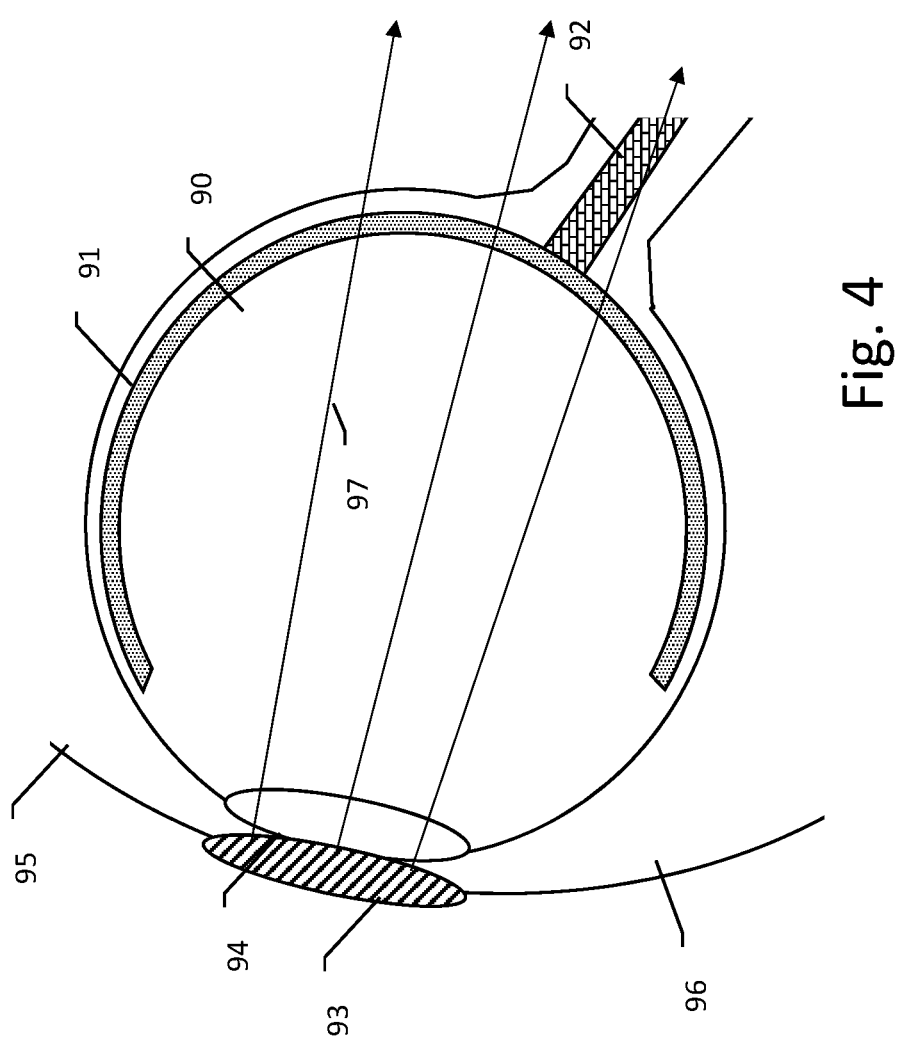

FIG. 4 shows another example, this time using a monopolar approach to stimulation of the eye. The patient's eye is shown at 90, with the retina generally at 91 and the optic nerve at 92. An electrode 93 is shown generally over the cornea 94, where the upper and lower eyelids 95, 96 meet. In other examples, the electrode 320 may be placed higher or lower to allow the patient to at least partly open his or her eye during the therapy, such as with placement on the upper or lower eyelid, the canthus or conjunctiva, or elsewhere near the eye. In this example, the field lines 97 extend into the eye, meaning that current flow as well as the effect of the electric field will extend more deeply into the eye, possibly increasing the effects at the retina 91 and/or near the optic nerve 92. The impedance encountered will be higher with this monopolar approach, and care must be taken to ensure that the edges or other features of the electrode 94 do not create concentrations of current that can be harmful or uncomfortable to the patient.

Some examples will use the bipolar approach of FIG. 3, and others may use the monopolar approach of FIG. 4. In some examples, diagnostics of the therapy, such as determinations of tissue interface impedance, may be measured using a bipolar approach, while therapy is delivered using the monopolar approach. For example, using a setup as in FIG. 3, checking whether the electrode patches are well attached to the tissue may be determined using lower amplitude outputs in a bipolar mode, and therapy may be delivered by placing the electrodes 74, 76 electrically in common with one another to deliver current relative to an indifferent electrode in a manner similar to that of FIG. 4.

Another approach to a combination therapy may be to deliver two different types of therapy to a patient each using electrical signals, such as by delivering a first therapy that targets the front of the eye by using electrode combinations that are located on the patients face, near the eye, such as on the eyelid, canthus, conjunctiva, cheek, nose, temple or forehead as shown in FIG. 3, interspersed, such as by cycling between therapy types or by the use of a pattern of stimulation that varies the electrode selection from pulse to pulse, with a second therapy directed deeper in the eye, using a remote electrode distant from the front of the eye, as shown in FIG. 3. For example, the first therapy may stimulate fluid flow at the front of the eye to reduce intraocular pressure and thereby treat glaucoma, while a second therapy stimulates cellular activity at the maculae or retina to thereby arrest the progress of, reverse, or otherwise treat macular degeneration.

Figure 5:
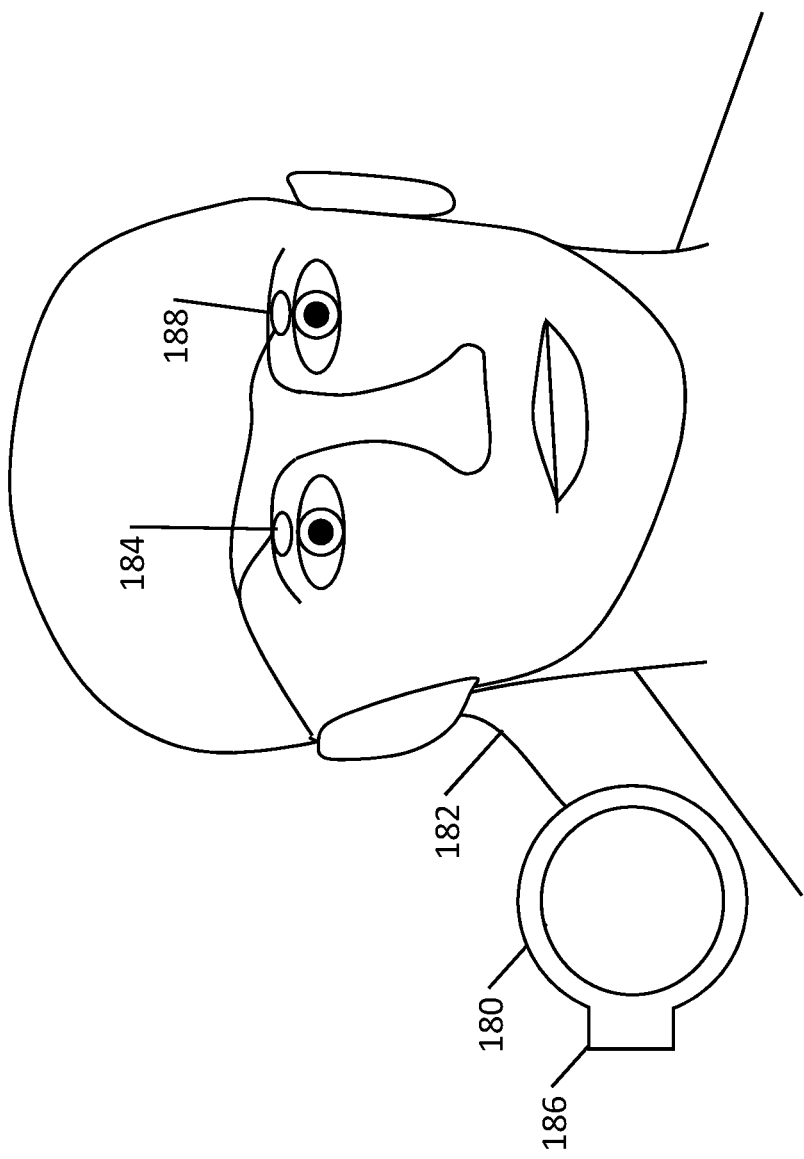
FIGS. 5-6 show illustrative therapy systems as applied to patients.
Figure 6:
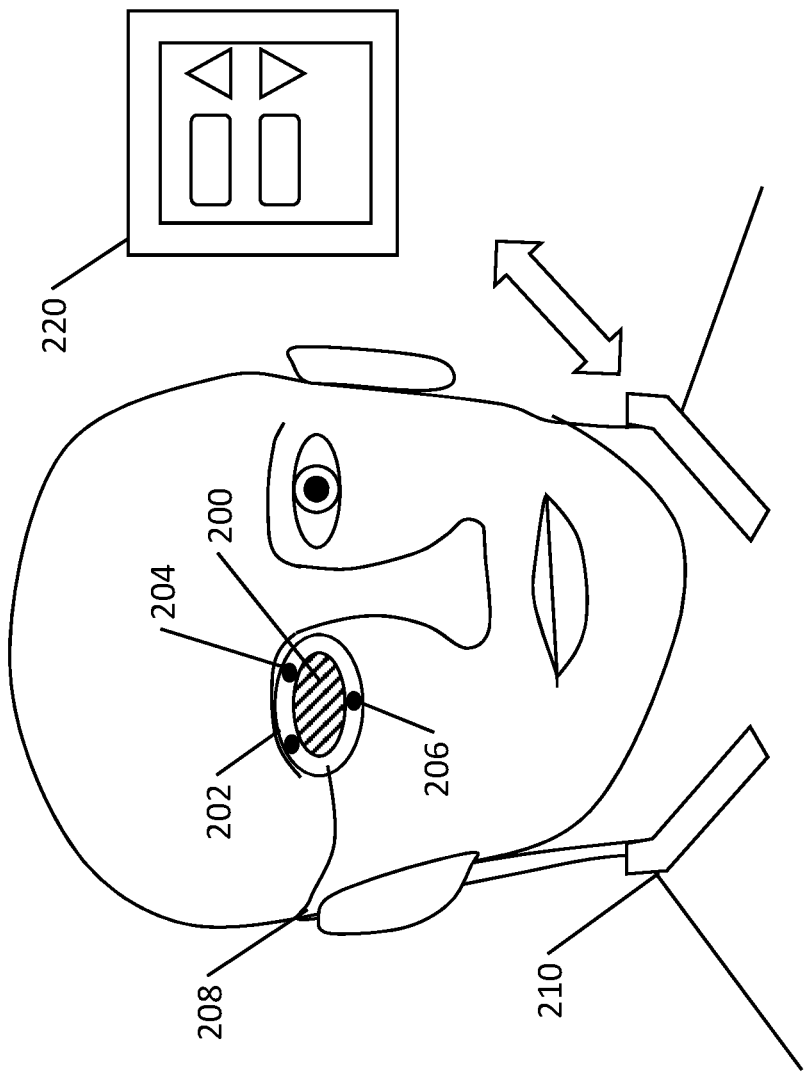

FIGS. 5-6 show illustrative examples of wearable therapy systems. Referring first to FIG. 5, the patient is shown with small electrode patches 184, 188 on the upper eyelids, coupled via wire 182, connecting to a cuff 180 that may carry a return electrode as well as a circuit module 186 that carries the pulse generator. In the example of FIG. 5, the cuff 186 may be worn, for example, on the arm. In FIG. 6, the patient is shown wearing an eyepatch 200 which includes a perimeter 202 having electrodes 204, 206 thereon, coupled by wire 208 to a pulse generator 210 worn on the neck of the patient. The pulse generator 210 may have a return electrode thereon or may couple separately to a return electrode worn elsewhere (not shown). The pulse generator 210 may communicate wirelessly, such as by Bluetooth, to a patient controller 220 having a user interface with suitable features, such as a touchscreen displaying control icons, or a set of tactile controls such as buttons, thereon, for turning therapy on or off or increasing or decreasing amplitude or intensity of the stimulation. As noted previously, in other examples, the wearable electrodes and pulse generator may be as shown in U.S. Prov. Pat. Apps. 62/774,093, 62/832,134, 62/861,658, 62/867,421, 62/873,450, and/or 62/884,890, the disclosures of which are incorporated herein by reference.

Figure 7:
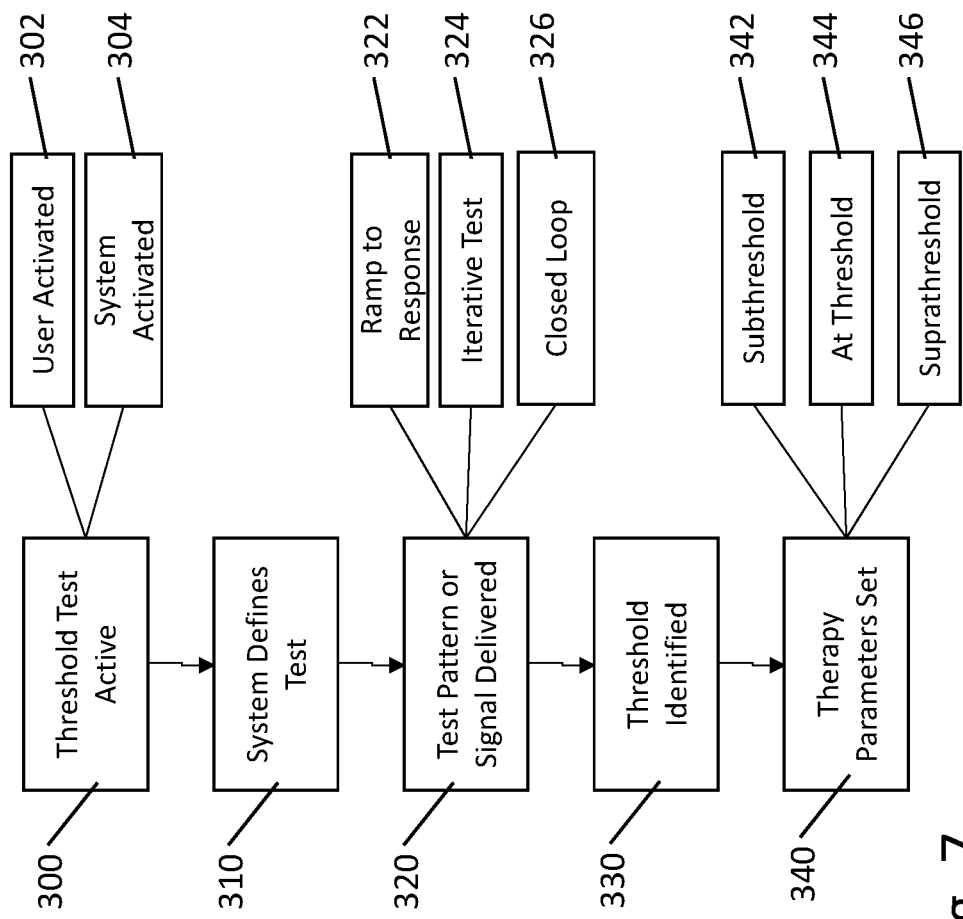

FIG. 7 shows process flow for an illustrative example. First, a phosphene threshold test 300 is activated. The test activation may be user activated as indicated at 302 by a user or patient selecting to perform a phosphene threshold test, or by a physician triggering such a step when fitting or prescribing a therapy system to a patient, or following up on a fitted or prescribed system with a patient. For example, a user controller or physician programmer may be used to activate 302 the phosphene threshold test. In other examples such a test may be system activated, as indicated at 304. The system may activate 304 phosphene testing at a defined interval or occasion, such as by activating the phosphene threshold test prior to each therapy session, or after a predefined number of sessions (such as a weekly test), or in response to a defined event such as a post-therapy session patient interaction finding that the patient is not responding to therapy or has not observed effects of therapy. For example, the patient may not improve in, or may experience deteriorating performance on a visual acuity test, or the patient may report difficulty seeing in day to day tasks, causing the system to automatically activate 304 a phosphene threshold test.

Next, optionally, the system may define the phosphene test 310. In some examples, the phosphene threshold test to be performed may use, as a starting point, therapy parameters that are in use, in which case the system can define the phosphene threshold test such as by setting test parameters (amplitude, pulse width, and/or frequency, for example) in relation to the parameters that are in use. In an example, the test definition may use the same amplitude, pulse width and/or frequency as the therapy setting in use. In other examples, the phosphene threshold test may be predefined by the system, such as by starting with a fixed frequency or pulse width and adjusting amplitude from a default low to high setting in a ramped sequence, for example.

The system then delivers a test pattern, as indicated at 320. A test pattern may be delivered after first performing safety and/or electrode placement tests, if desired and as shown in FIG. 8, below. The test pattern may, in one example, be a ramp-to-response pattern, as indicated at 322. Within the pattern 322, the patient may receive an electrical therapy signal that begins at a low amplitude or pulse width, and which is then increased gradually until the patient observes and reports the occurrence of phosphenes. The patient may, for example, speak into a microphone of a pulse generator or patient controller, or press a button on a patient controller or on the pulse generator, to indicate that the phosphene has been observed. The ramp to response mode may, as indicated, apply pulse width and or voltage as a variable, and the ramp to response mode 322 may be repeated to test different variables, such as by performing the test using a first pulse width and a varying voltage until the response is observed, and then fixing the voltage and varying pulse width from a short pulse width to a wide pulse width. In another example, the ramp to response may ramp voltage while using a first fixed pulse width, and, after receiving a response, ramp the voltage again while using a second fixed pulse width, thus allowing mapping of the patient's response across two variables. In other example, the frequency of stimulation may be varied, or ramping may be performed at more than one frequency. In an example where a carrier signal is modulated by a second, lower frequency (such as a 10 kHz square wave modulated by a 100 Hz square wave), the carrier or modulation frequencies may be varied, or multiple carrier and modulation frequencies may be tested. An iterative test 324 may be performed instead. Here, a set of parameters are tested for a period of time, and then stimulus stops to allow the user to be interrogated. Following user interrogation, a different set of parameters may be tested. Such an approach may be useful where the patient has difficulty with immediately responding to the received signals.

A closed loop test 326 may be performed instead. When a phosphene is generated, the system may sense the occurrence of the phosphene by observing neural signaling that is generated by the optic nerve in response to the phosphene, which is transmitted to the brain of the patient. A closed loop test would not necessarily rely upon the voluntary response of the patient to the stimulus, potentially making a more reliable test.

When phosphenes are observed, the system can observe that the combination of parameters that is associated with phosphene observation form a phosphene threshold. It should be understood that some patients may experience phosphene thresholds that are defined by a plurality of factors, including which electordes are in use, amplitude of the signal, pulse width, and frequency of the signal. Thresholds may be defined as a single threshold in a system that holds some variable fixed, such as by using a single frequency and pulse width, with a single combination of output electrodes, to define the phosphene threshold one dimensionally in terms of signal amplitude. In other examples several thresholds may be defined for different combinations of electrode selection, frequency, pulse width, pulse shape, or other factors. Each of these ways of defining the phosphene threshold may be performed within element 330.

Therapy parameters are then set, as indicated at 340. Therapy parameters may take several forms. In some examples, subthreshold stimulus may be applied as indicated at 342, by, for example, reducing therapy amplitude (current, voltage or power, for example) at some percentage of the determined threshold, such as a 75%, 80%, 85%, 90%, 95%, or 99% of the determined threshold. A subthreshold therapy 342, set close to but below the phosphene threshold, may allow the user to perform other activities during therapy without phosphenes interfering with vision, such that user may perform light chores, exercise, or watch television, for example. In other examples, therapy may be delivered at the threshold 344, or at suprathreshold levels 346, as it may be that the phosphenes themselves, representing firing of the neural system in the eye, aid in ensuring beneficial cellular responses to the disease condition. A suprathreshold therapy level may be, for example, 110%, 125%, 150%, 200% or other level set relative to the phosphene threshold, with the percentage referring to output amplitude, pulse width, or both. In other example, frequency or other parameter, such as slew rate, may be adjusted as well.

Some illustrative embodiments comprise systems configured for treating a patient having a vision disorder comprising configured for treating a patient having a vision disorder comprising a pulse generator (FIG. 2, 100) and a plurality of electrodes electrically (FIG. 2, 162, 164, 166) coupled to the pulse generator, the pulse generator comprising output means for issuing therapy pulses to a patient using the electrodes (FIG. 2, 160, having for example, voltage or control regulating circuitry to increase or decrease amplitudes relative to a power supply 130 and associated switches to directed electrical energy to the electrodes); control means for controlling the output means (FIG. 2, 110, which may include a microcontroller, microprocessor, or state machine operably linked to memory that contains machine readable operating instructions, as well as any associated analog or digital sub-circuits, ASICs, etc. to process incoming and/or outgoing signals), the control means configured to deliver one or more therapy routines to the patient according to one or more stored instruction sets (again, such instruction sets can be stored in a memory within the pulse generator or may be accessible using a communication circuit 140 to retrieve or receive instructions); threshold test means for performing a phosphene threshold test and determining threshold parameters of a therapy routine that will cause the patient to experience phosphenes, the phosphene threshold test comprising delivering threshold test pulses using the output means using threshold test parameters including one or more of pulse width, amplitude and frequency (such threshold test means may comprise stored instruction sets on machine readable media, such as a memory stored in the pulse generator or stored on a patient device such as a patient interface 30 or patient controller 220 and accessible via a communication circuit 140 to retrieve or receive instructions); and configuration means that configures at least one therapy routine using the determined threshold parameters (such threshold test means may comprise stored instruction sets on machine readable media performing one or more of blocks 300, 310, 320, 330 of FIG. 7, such as a memory stored in the pulse generator or stored on a patient device such as a patient interface 30 or patient controller 220, or still further remote and accessible via cellular, broadband or internet resources as stored on a manufacturer interface 50 or physician interface 60, and accessible via a communication circuit 140 to retrieve or receive instructions). Additionally or alternatively, the system comprises storage means for storing at least one executable instruction set defining a therapy routine (such storage means being a machine readable memory in a pulse generator, patient controller, or manufacturer or physician interface), wherein the threshold test means is configured to access the stored executable instruction set to define at least one of the frequency, amplitude and pulse width of the threshold test pulses. Additionally or alternatively, the threshold test means is configured to vary the threshold test pulses to ramp (322 of FIG. 7) from a first energy level to a second, relatively higher energy level until phosphenes occur. Additionally or alternatively, the system comprises a user interface to receive a patient indication that the patient has experienced a phosphene (such as patient interface 30 or patient controller 220, or provided on a patient coupling device 20; a button, touchscreen, microphone or accelerometer responsive to patient movement may serve to receive the patient input by pressing or actuating a button, touchscreen, an icon on a touchscreen, or speaking into a microphone, or shaking the head or hand or blinking to actuate the accelerometer). The system may include one or more electrodes placed near the eye for sensing the occurrence of phosphenes by electrically receiving a signal indicative of a phosphene (performing as indicated at 326 in FIG. 7; this may be captured using a feedback circuit 14 or 150, for example). Additionally or alternatively, the configuration means sets therapy delivery parameters of the therapy routine below, approximately at, or above the determined phosphene threshold. Additionally or alternatively, the system comprises a user interface (such as interface 30 or patient controller 220), wherein the threshold test means is configured to perform the phosphene threshold test in a series of iterations (block 324 in FIG. 7) in which: A. a phosphene threshold test signal is issued; and B. the patient is queried via the user interface as to whether a phosphene was observed and a response from the patient is obtained via the user interface; wherein if the patient indicates that no phosphene was observed at B, the phosphene threshold test signal is modified and the iterative analysis returns to A; or if the patient indicates that a phosphene was observed, the system concludes that the last used parameters of the phosphene threshold test signal met the phosphene threshold. Additionally or alternatively, at least one of the pair of the electrodes is carried on an eyepiece that is worn about the eye, as in any of FIGS. 3-6. Additionally or alternatively, at least one of the pair of the electrodes is carried on a headpiece that is worn on the head of the patient, as shown at 200 in FIG. 6, or as shown in U.S. Prov. Pat. Apps. 62/774,093, 62/832,134, 62/861,658, 62/867,421, 62/873,450, and/or 62/884,890, the disclosures of which are incorporated herein by reference.

FIG. 8 shows an illustrative method that may be performed by a system as disclosed herein. The illustrative method may be for treating, arresting, and/or reversing disease progress in a patient having a vision disorder using a therapy delivery system. The method comprises delivering, from a pulse generator that is wearable or external to a patient an electrical output via one or more electrodes placed on the patient's skin over or near the eye, as indicated at 360. Next, following delivery of the electrical output, the method includes presenting a visual performance test via the therapy delivery system to the user, as indicated at 362. As the patient performs the test, or in response to performance of the test, the system, as part of the method, next records, the patient's performance on the performance test, as indicated at 364. Optionally, the method may further include with the therapy delivery system, whether the patient's performance on the visual performance test meets a threshold for performance and, if the patient's performance does not meet the threshold for performance, modifying one or more therapy delivery parameters used while delivering the electrical output, as indicated at 366. Within the method of FIG. 8, the therapy may comprise a plurality of electrical pulses, and the delivery parameters include at least one of a pulse width, frequency and an amplitude, and modification of the one or more therapy delivery parameters at 366 may include adjusting at least one of the pulse width, frequency and amplitude. In an example, the therapy delivery system comprises a wearable eyepiece having a display that is visible to the patient when worn, and the visual performance test at 362 may be performed/displayed using the eyepiece. In another example, the therapy delivery system comprises a user controller having a display, and the visual performance test of block 362 may be performed/displayed using the display. The therapy may be monopolar (using one electrode near the eye such as on the eyelid or palpebra, and one electrode located elsewhere such as behind the ear, on the neck or on the torso or a limb), or it may be bipolar (using two electrodes as anode and cathode with both located near the eye, such as on the eyelids or palpebral).

Some illustrative embodiments comprise systems configured for treating a patient having a vision disorder comprising a pulse generator (FIG. 2, 100) and a plurality of electrodes electrically (FIG. 2, 162, 164, 166) coupled to the pulse generator, the pulse generator comprising output means for issuing therapy pulses to a patient using the electrodes (FIG. 2, 160, having for example, voltage or control regulating circuitry to increase or decrease amplitudes relative to a power supply 130 and associated switches to directed electrical energy to the electrodes); control means for controlling the output means (FIG. 2, 110, which may include a microcontroller, microprocessor, or state machine operably linked to memory that contains machine readable operating instructions, as well as any associated analog or digital sub-circuits, ASICs, etc. to process incoming and/or outgoing signals), the control means configured to deliver one or more therapy routines to the patient according to one or more stored instruction sets (again, such instruction sets can be stored in a memory within the pulse generator or may be accessible using a communication circuit 140 to retrieve or receive instructions); user interface means for displaying one or more images to the patient and receiving an input from the patient (FIG. 1, at 30, FIG. 6 at 220, where the user interface means may include for example a touchscreen, buttons, lights, etc. as needed and may take the form of a tablet computer, smartphone, handheld device, etc.); recording means for recording user performance on a visual performance test administered to the patient using the user interface means following the delivery of a therapy routine (such recording means may take the form of a read/write memory in the user interface means, internet-based and remote cloud storage, and/or a memory of the pulse generator). Additionally or alternatively, the system may also include determining means adapted to determine whether the patient's performance on the visual performance test meets a threshold for performance (such determining means may be comprised of a machine readable memory storing operable instruction sets that compare patient response to a visual test to outcome measures for such tests, applying, for example, a Snellen test, a random E test, a kinetic field test, a Goldmann test, an Amsler test, a Humphrey test, or other tests for contrast, visual acuity, visual field, tracking, color, brightness, peripheral field), and adjustment means to adjust one or more parameters of the therapy routine in response to a determination that the patient's performance does not meet the threshold for performance (the adjustment means may comprise machine readable memory storing operable instruction sets to changing parameters of the therapy routine, such as by changing pulse width, amplitude, frequency, duty cycle, pulse shape or any other suitable feature, such as duration). Additionally or alternatively, the determining means may instead make use of a communications modality to send data related to a patient's performance to a remote workstation where a physician or trained personnel may judge the performance, or to a central server where artificial intelligence may be used to judge the performance, such as by communicating via cellular, broadband, or internet services. Additionally or alternatively, the therapy routine comprises a plurality of electrical pulses and the parameters of the therapy routine include at least one of pulse width, frequency and amplitude, such that the adjustment means is configured to change at least one of pulse width, frequency and amplitude. Additionally or alternatively, at least one of the pair of the electrodes is carried on an eyepiece that is worn about the eye, as in any of FIGS. 3-6, and/or at least one of the pair of the electrodes is carried on a headpiece that is worn on the head of the patient, as shown at 200 in FIG. 6, and/or as shown in U.S. Prov. Pat. Apps. 62/774,093, 62/832,134, 62/861,658, 62/867,421, 62/873,450, and/or 62/884,890, the disclosures of which are incorporated herein by reference.

FIG. 9 shows an illustrative method that may be performed by a system as disclosed herein. The method may be for treating, arresting, and/or reversing disease progress in a patient having a vision disorder. In the example, the method is performed while the patient is wearing or otherwise in contact with a plurality of therapy delivery electrodes coupled to a pulse generator and forming part of a therapy delivery system. The illustrative method comprises the pulse generator determining whether at least a pair of the plurality of therapy delivery electrodes are safely coupled to the patient, as indicated at 380. Such testing may comprise checking the impedance or other coupling characteristics, such as temperature, of the electrodes to patient tissue and comparing measured parameters to predetermined thresholds. Next, if the electrodes are safely coupled, the pulse generator issues an electrical therapy output to the at least a pair of the therapy delivery electrodes, as indicated at 382. Otherwise, the therapy delivery system alerting the patient that the electrodes require repositioning, as indicated at 384.

Within FIG. 9, block 380 may comprise the pulse generator monitoring an impedance between the electrodes and determining whether the impedance is within a desired range, wherein if the monitored impedance is out of the desired range, the pulse generator determines that the electrodes are not safely coupled to the patient. In another example, the issuance of therapy at 382 may include the pulse generator measuring impedance encountered by the electrical therapy output and determining whether the electrical therapy output was delivered to target tissue of the patient by calculating whether the encountered impedance is within a target range. Generally in FIG. 9, at least one of the pair of the plurality of therapy delivery electrodes is carried on an eyepiece that is worn about the eye. Additionally or alternatively, at least one of the pair of the plurality of therapy delivery electrodes is carried on a headpiece that is worn on the head of the patient. For the method of FIG. 9, the therapy delivery system may further comprise a patient controller configured to wirelessly communicate with the pulse generator, and the alert, if any, of block 384, is issued by the patient controller. The therapy may be monopolar (using one electrode near the eye such as on the eyelid or palpebra, and one electrode located elsewhere such as behind the ear, on the neck or on the torso or a limb), or it may be bipolar (using two electrodes as anode and cathode with both located near the eye, such as on the eyelids or palpebral).

Some illustrative embodiments comprise a system configured for treating a patient having a vision disorder comprising a pulse generator (FIG. 2, 100) and a plurality of electrodes electrically (FIG. 2, 162, 164, 166) coupled to the pulse generator, the pulse generator comprising output means for issuing therapy pulses to a patient using the electrodes (FIG. 2, 160, having for example, voltage or control regulating circuitry to increase or decrease amplitudes relative to a power supply 130 and associated switches to directed electrical energy to the electrodes); control means for controlling the output means (FIG. 2, 110, which may include a microcontroller, microprocessor, or state machine operably linked to memory that contains machine readable operating instructions, as well as any associated analog or digital sub-circuits, ASICs, etc. to process incoming and/or outgoing signals), the control means configured to deliver one or more therapy routines to the patient according to one or more stored instruction sets (again, such instruction sets can be stored in a memory within the pulse generator or may be accessible using a communication circuit 140 to retrieve or receive instructions); feedback means to obtain feedback from the electrodes (FIG. 2, 150, which may include buffering, filtering and sampling circuitry to receive incoming signals and extract usable information such as the voltage or current that is sensed by or passes through the electrodes 162, 164, 166 before, during and/or after therapy, as well as receiving non-electrical physiological data such as motion, sound, light and/or chemical signals or phenomena); wherein the control means is configured to execute a stored instruction set to deliver a therapy routine by first determining, using information from the feedback means, whether at least a pair of the electrodes are safely coupled to the patient (FIG. 9, block 380) and: if so, to direct the output means to issue therapy pulses to the patient using at least the pair of electrodes (FIG. 9, block 382); or if not, to alert the patient that the electrodes require repositioning (FIG. 9, block 384, where the alert may be issued by a sound warning, a light, a message on a screen of the pulse generator or associated patient programmer such as shown above at 220 in FIG. 6 or via a patient interface 30 in FIG. 1). Additionally or alternatively, the control means is configured to obtain impedance information from the feedback means to determine whether the electrodes are coupled to the patient, and then to determine whether the impedance is within a desired range, wherein if the monitored impedance is out of the desired range, the control means determines that the electrodes are not safely coupled to the patient. Additionally or alternatively, temperature may be used to determine coupling. Additionally or alternatively, the control means, when executing the stored instruction set, further obtains from the feedback means impedance information during issuance of the therapy pulses to determine whether the electrical therapy output was delivered to target tissue of the patient by calculating whether the encountered impedance is within a target range. Additionally or alternatively, at least one of the pair of the electrodes is carried on an eyepiece that is worn about the eye, as in any of FIGS. 3-6. Additionally or alternatively, at least one of the pair of the electrodes is carried on a headpiece that is worn on the head of the patient, as shown at 200 in FIG. 6. As noted previously, the wearable electrodes may be as shown in U.S. Prov. Pat. Apps. 62/774,093, 62/832,134, 62/861,658, 62/867,421, 62/873,450, and/or 62/884,890, the disclosures of which are incorporated herein by reference.

While the above description primarily focuses on a wearable, non-invasive system, other examples may include an electrode or lead that extends into the patient, such as into the eye socket, to lie against the eye itself. In another example, an implantable system may be provided that has one or more electrodes on either side of the eye, or in back and front, or within the eye itself. Some implantable or semi-implantable systems may include one or more transducers to receive sonic, RF, or magnetic wave energy and convert to one or more of sonic or electrical waveforms to deliver therapy such as by providing an implantable seed that is attached in or on the eye, or near the eye, and receives an applied field energy and converts the field energy to a local stimulus, either in or near the retina.

The drawings illustrate generally, by way of example, but not by way of limitation, various embodiments discussed in the present document. The drawings are not necessarily to scale. The drawings show, by way of illustration, specific embodiments in which the invention can be practiced. Such examples can include elements in addition to those shown or described. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls. In this document, the terms "a" or "an" are used, as is common in patent documents, to include one or more than one, independent of any other instances or usages of "at least one" or "one or more." Moreover, in the following claims, the terms "first," "second," and "third," etc. are used merely as labels, and are not intended to impose numerical requirements on their objects.

Method examples described herein can be machine or computer-implemented at least in part. Some examples can include a computer-readable medium or machine-readable medium encoded with instructions operable to configure an electronic device to perform methods as described in the above examples. An implementation of such methods can include code, such as microcode, assembly language code, a higher-level language code, or the like. Such code can include computer readable instructions for performing various methods or method steps. The code may form portions of computer program products. Further, in an example, the code can be tangibly stored on one or more volatile, non-transitory, or non-volatile tangible computer-readable media, such as during execution or at other times. Examples of these tangible computer-readable media can include, but are not limited to, hard disks, removable magnetic or optical disks, magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments can be used, such as by one of ordinary skill in the art upon reviewing the above description. Various features may be grouped together to streamline the disclosure, however, this should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments can be combined with each other in various combinations or permutations. The scope of the invention should be determined with reference to the appended claims, along with the full scope of equivalents to which such claims are entitled.

What is claimed is:

1. A method of treating, arresting, and/or reversing disease progress in a patient having a vision disorder, the method being performed while the patient is wearing or otherwise in contact with a plurality of therapy delivery electrodes coupled to a pulse generator and forming part of a therapy delivery system, the method comprising:
   the pulse generator determining whether at least a pair of the plurality of therapy delivery electrodes are coupled to the patient; and
   if so, the pulse generator issuing a therapeutic electrical therapy output to at least one of the therapy delivery electrodes;
   if not, the therapy delivery system alerting the patient that the electrodes require repositioning;
   wherein the step of the pulse generator determining whether the electrodes are coupled to the patient comprises the pulse generator:
      applying a test pulse to the patient using the pair of the plurality of the therapy delivery electrodes;
      during the test pulse, monitoring an impedance between the pair of the therapy delivery electrodes; and
      determining whether the impedance is within a desired range,
      wherein if the impedance is out of the desired range, the pulse generator is configured to determine the electrodes are not safely coupled to the patient;
   further wherein:
   the plurality of therapy delivery electrodes includes first and second electrodes for placement near the eyes of the patient, and an indifferent electrode;
   the first and second electrodes are used to deliver the test pulse; and
   the therapeutic electrical therapy output is delivered using the indifferent electrode and one of the first or second electrodes.

2. The method of claim 1 further comprising the pulse generator measuring impedance encountered by the therapeutic electrical therapy output and determining whether the electrical therapy output was delivered to target tissue of the patient by calculating whether the encountered impedance is within a target range.

3. The method of claim 1 wherein at least one of the pair of the plurality of therapy delivery electrodes is carried on an eyepiece that is worn about the eye.

4. The method of claim 1 wherein at least one of the pair of the plurality of therapy delivery electrodes is carried on a headpiece that is worn on the head of the patient.

5. The method of claim 1 wherein the therapy delivery system further comprises a patient controller configured to wirelessly communicate with the pulse generator, and the alert, if any, is issued by the patient controller.

6. The method of claim 1 wherein:
   the test pulse has a first pulse width;
   the therapeutic electrical therapy output comprises at least one therapy pulse having a second pulse width; and
   the first pulse width is shorter than the second pulse width.

7. The method of claim 1 wherein:
   the test pulse has a first amplitude;
   the therapeutic electrical therapy output comprises at least one therapy pulse having a second amplitude; and
   the first amplitude is less than the second amplitude.

8. The method of claim 1 wherein the step of the pulse generator issuing a therapeutic electrical therapy output to at least one of the therapy delivery electrodes is performed as part of a therapy regimen comprising repeatedly delivering therapeutic electrical therapy output and includes, at least once:
   delivering the test pulse between deliveries of the therapeutic electrical therapy output;
   during the test pulse, monitoring impedance between the pair of the therapy delivery electrodes; and
   determining whether the impedance is within a target range,
   wherein if the impedance is not in the target range, the method comprises issuing an alert to the patient and stopping the therapy regimen; and
   if the impedance is in the target range, continuing the therapy regimen.

9. A system for treating a patient having a vision disorder comprising:
   a pulse generator having therein output circuitry for generating output pulses and configured to selectively provide an alert to the patient; and
   a plurality of therapy delivery electrodes coupled to the pulse generator, wherein the output circuitry is configured to generate the output pulses using the therapy delivery electrodes, and the pulse generator comprises sensing circuitry configured to sense parameters related to the therapy delivery electrodes; wherein the pulse generator is configured to perform the following:
   the pulse generator using the sensing circuitry to determine whether at least a pair of the plurality of therapy delivery electrodes are safely coupled to the patient by:
      applying a test pulse to the patient using the pair of the plurality of the therapy delivery electrodes;
      during the test pulse, monitoring an impedance between the pair of the therapy delivery electrodes; and
      determining whether the impedance is within a desired range,
      wherein if the impedance is not in the desired range, the pulse generator is configured to determine the electrodes are not safely coupled to the patient; and if so, the pulse generator using the output circuitry to generate a therapeutic electrical output to the at least one of the pair of the therapy delivery electrodes;

if not, the pulse generator alerting the patient that the electrodes require repositioning;

further wherein:

the plurality of therapy delivery electrodes includes first and second electrodes for placement near the eyes of the patient, and an indifferent electrode;

the first and second electrodes are used to deliver the test pulse; and the therapeutic electrical therapy output is delivered using the indifferent electrode and one of the first or second electrodes.

10. The system of claim 9 wherein the sensing circuitry is configured to measure impedance encountered by the therapeutic electrical output and determine whether the electrical therapy output was delivered to target tissue of the patient by calculating whether the encountered impedance is within a target range.

11. The system of claim 9, further comprising an eyepiece that is worn about the eye, wherein the electrodes are carried on the eyepiece.

12. The system of claim 9, further comprising a headpiece configured to be worn on the head of the patient, wherein at least one of the therapy delivery electrodes is carried on the headpiece.

13. The system of claim 9, further comprising a patient controller configured to wirelessly communicate with the pulse generator, and the alert, if any, is issued by the patient controller responsive to a wireless communication from the pulse generator.

14. The system of claim 9 wherein:

the test pulse has a first pulse width;

the therapeutic electrical therapy output comprises at least one therapy pulse having a second pulse width; and the first pulse width is shorter than the second pulse width.

15. The system of claim 9 wherein:

the test pulse has a first amplitude;

the therapeutic electrical therapy output comprises at least one therapy pulse having a second amplitude; and the first amplitude is less than the second amplitude.

* * * * *